US011054426B2

(12) United States Patent
Galloway et al.

(10) Patent No.: US 11,054,426 B2
(45) Date of Patent: *Jul. 6, 2021

(54) DIAGNOSTIC METHOD

(71) Applicant: Cytosystems Ltd, York (GB)

(72) Inventors: David Galloway, Aberdeen (GB); Nick Coleman, Cambridge (GB)

(*) Notice: Subject to any disclaimer, the term of this patent is extended or adjusted under 35 U.S.C. 154(b) by 337 days.

This patent is subject to a terminal disclaimer.

(21) Appl. No.: 16/168,096

(22) Filed: Oct. 23, 2018

(65) Prior Publication Data

US 2019/0056401 A1 Feb. 21, 2019

Related U.S. Application Data

(63) Continuation-in-part of application No. 13/512,585, filed as application No. PCT/GB2012/000008 on Jan. 6, 2012, now Pat. No. 10,107,814.

(30) Foreign Application Priority Data

Jan. 7, 2011 (GB) ..................................... 1100223

(51) Int. Cl.
*G01N 33/50* (2006.01)
*G01N 33/574* (2006.01)

(52) U.S. Cl.
CPC .. *G01N 33/57407* (2013.01); *G01N 2333/914* (2013.01); *G01N 2800/54* (2013.01)

(58) Field of Classification Search
CPC .............................................. G01N 2333/914
USPC ....................................................... 435/7.23
See application file for complete search history.

(56) References Cited

U.S. PATENT DOCUMENTS

| 6,303,323 B1 | 10/2001 | Laskey | 435/7.23 |
| 7,056,690 B2 | 6/2006 | Laskey et al. | 435/7.23 |
| 10,107,814 B2 * | 10/2018 | Galloway | G01N 33/57407 |

FOREIGN PATENT DOCUMENTS

WO WO 2006/116327 A1 11/2006 ........... G01N 33/483

OTHER PUBLICATIONS

Brems-Eskildsen, Anne Sofie, et al., "Prediction and Diagnosis of Bladder Cancer Recurrence Based on Urinary Content of hTERT, SENP1, PPP1CA and MCM5 Transcripts," BMC Cancer, vol. 10, No. 1, p. 646, Nov. 24, 2010.
Burger, M., et al., "Mcm2 Predicts Recurrence Hazard in Stage Ta/T1 Bladder Cancer More Accurately than CK20, Ki67 and Histological Grade," British J. of Cancer, vol. 96, No. 11, p. 1711-1715, May 15, 2007.
Korkolopoulou, P., et al., "Minichromosome Maintenance Proteins 2 and 5 Expression in Muscle-Invasive Urothelial Cancer: A Multivariate Survival Study Including Proliferation Markers and Cell Cycle Regulators," Human Pathology, vol. 36, No. 8, p. 899-907, Aug. 1, 2005.
Krüger, S., et al., "Prognostic Value of MCM2 Immunoreactivity in Stage T1 Transitional Cell Carcinoma of the Bladder," European Urology, vol. 43, No. 2, p. 138-145, Feb. 1, 2003.
Proctor, Ian, et al., "Biomarkers in Bladder Cancer," Histopathology, vol. 57, No. 1, p. 1-13, Jun. 23, 2010.
Stoeber, K. et al., "Immunoassay for Urothelial Cancers that Detects DNA Replication Protein Mcm5 in Urine," The Lance, vol. 354, No. 9189, p. 1524-1525, Oct. 30, 1999.
Stoeber, K. et al., "Diagnosis of Genito-Urinary Tract Cancer by Detection of Minichromosome Maintenance 5 Protein in Urine Sediments," J. of the National Cancer Institute, vol. 94, No. 14, p. 1071-1079, Jul. 17, 2002.
Tockman et al (Cancer Res., 1992, 522711s-2718s).
Stoeber et al (Journal of the National Cancer Institute, 2002, 94(14): 1071-1079).
Sanchez-Carbayo et al (Cancer, 2001, 92(11): 2811-2819).
Pajor et al (Cytometry Part A, 2008, 73A: 259-265).

* cited by examiner

*Primary Examiner* — Sean E Aeder
(74) *Attorney, Agent, or Firm* — BioPatent

(57) ABSTRACT

The invention provides a method of detecting a subject suffering from, or at risk of suffering from, bladder cancer the method comprising
  i) providing a body fluid sample isolated from a subject;
  ii) isolating cells from said sample to provide a cell sample;
  iii) contacting the sample with a specific binding member capable of binding to a minichromosome maintenance (MCM) polypeptide(s);
  iv) determining the binding of said specific binding member to the cell sample;
  v) counting those cells in said cell sample which bound to said specific binding member to provide a cell count;
  vi) determining, based on the cell count, whether the subject has, or is at risk of having, bladder cancer.

9 Claims, 24 Drawing Sheets

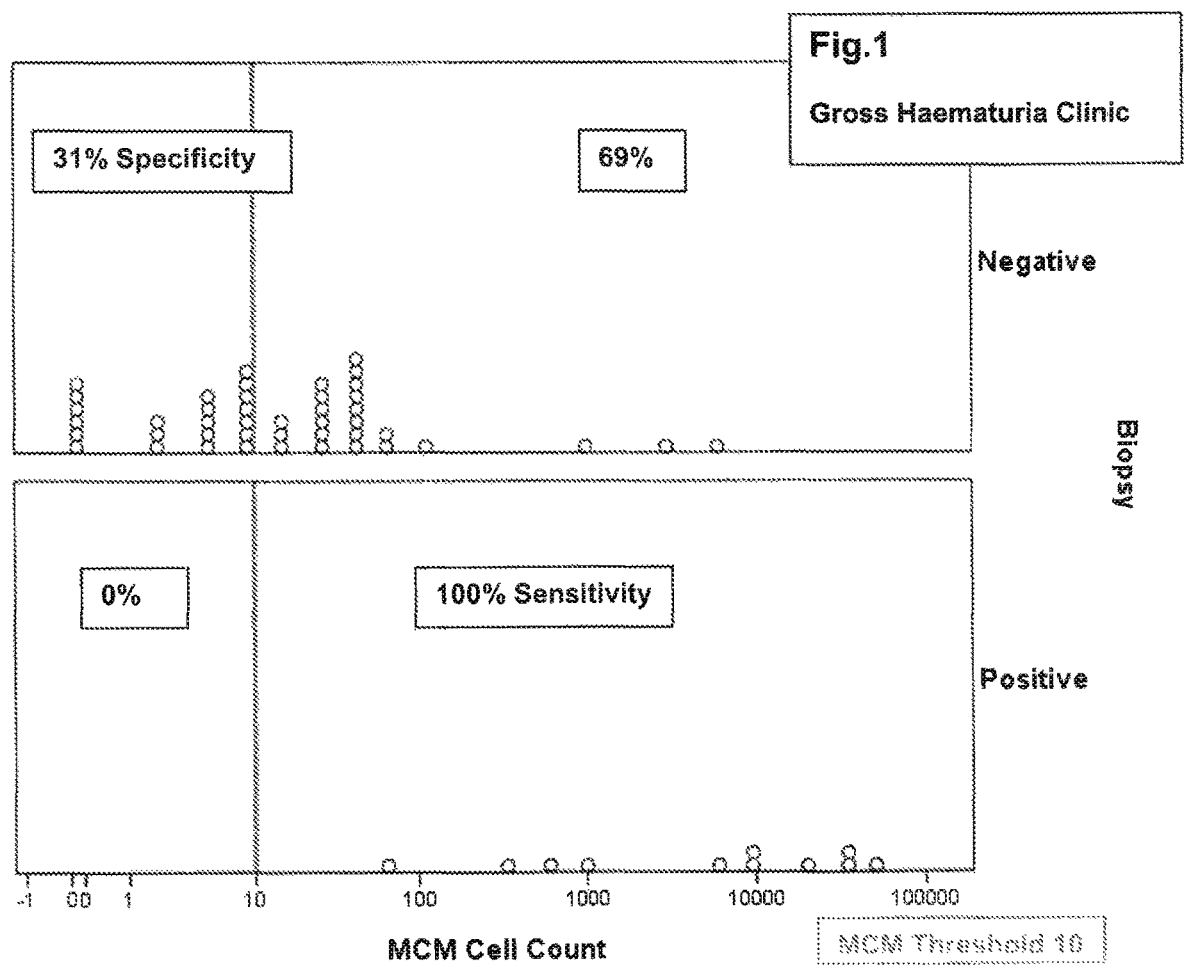

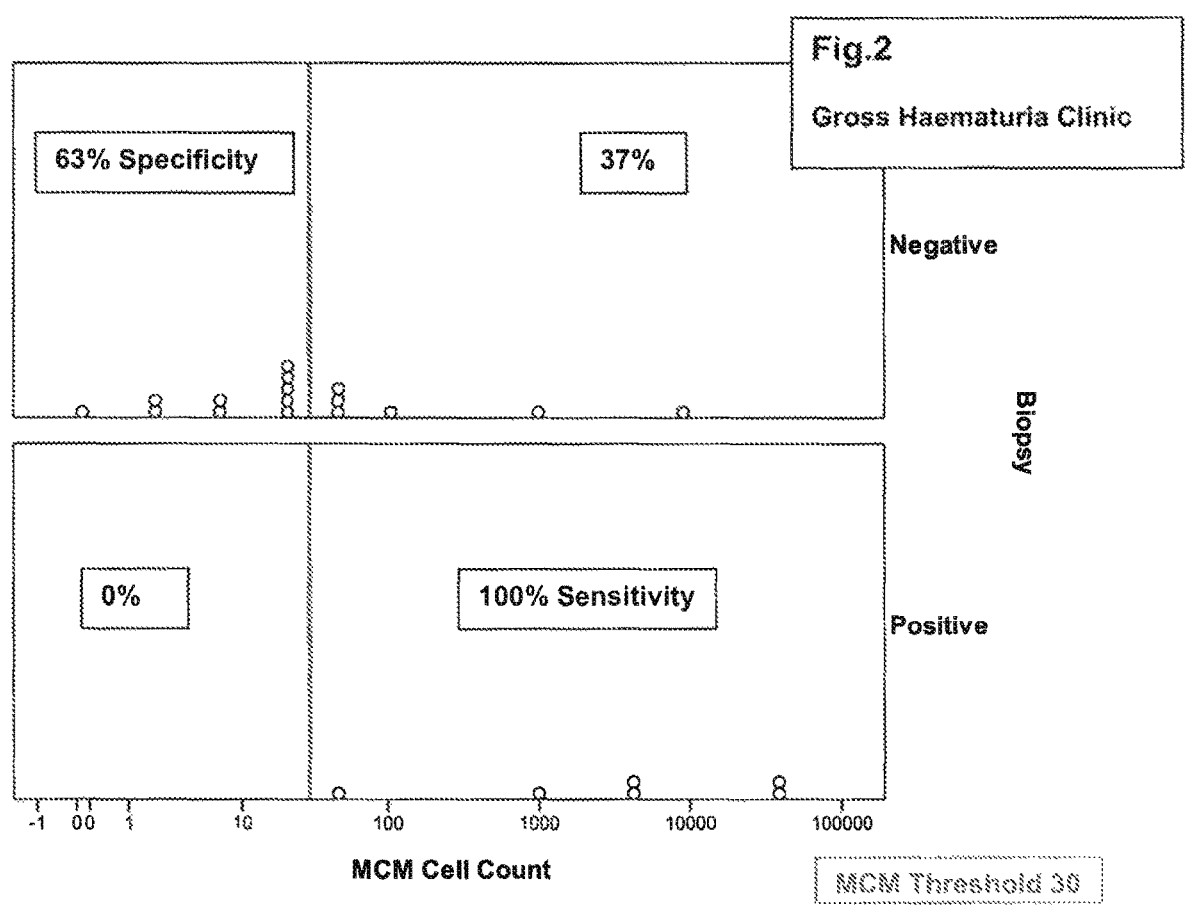

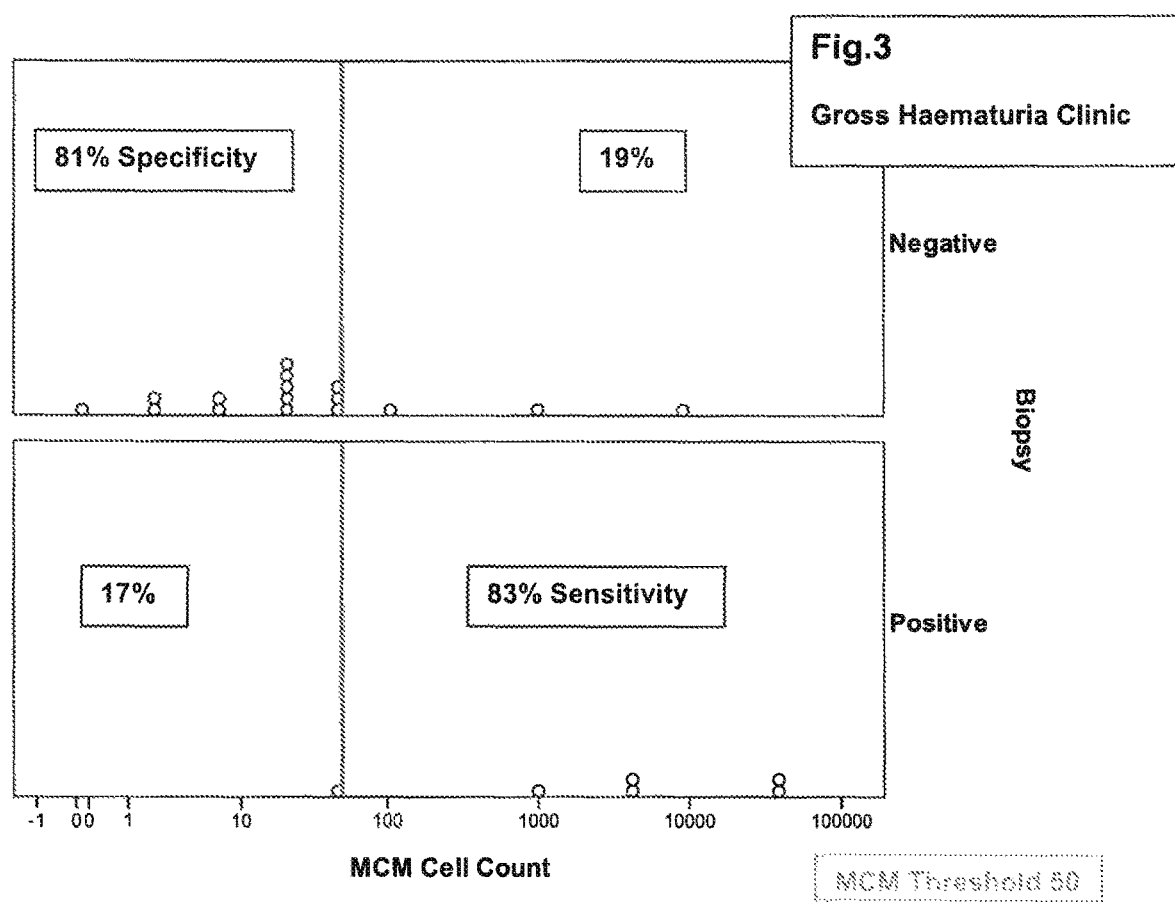

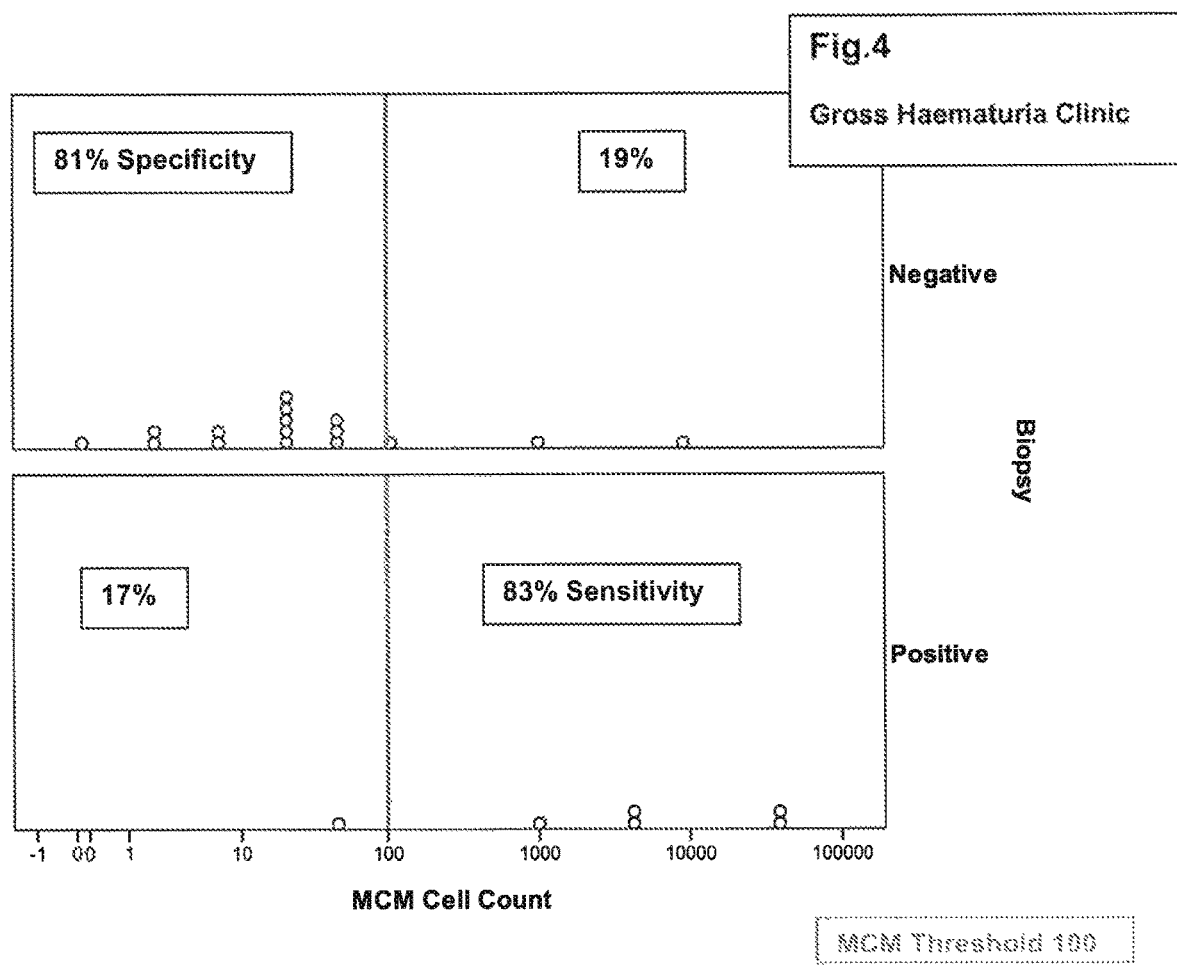

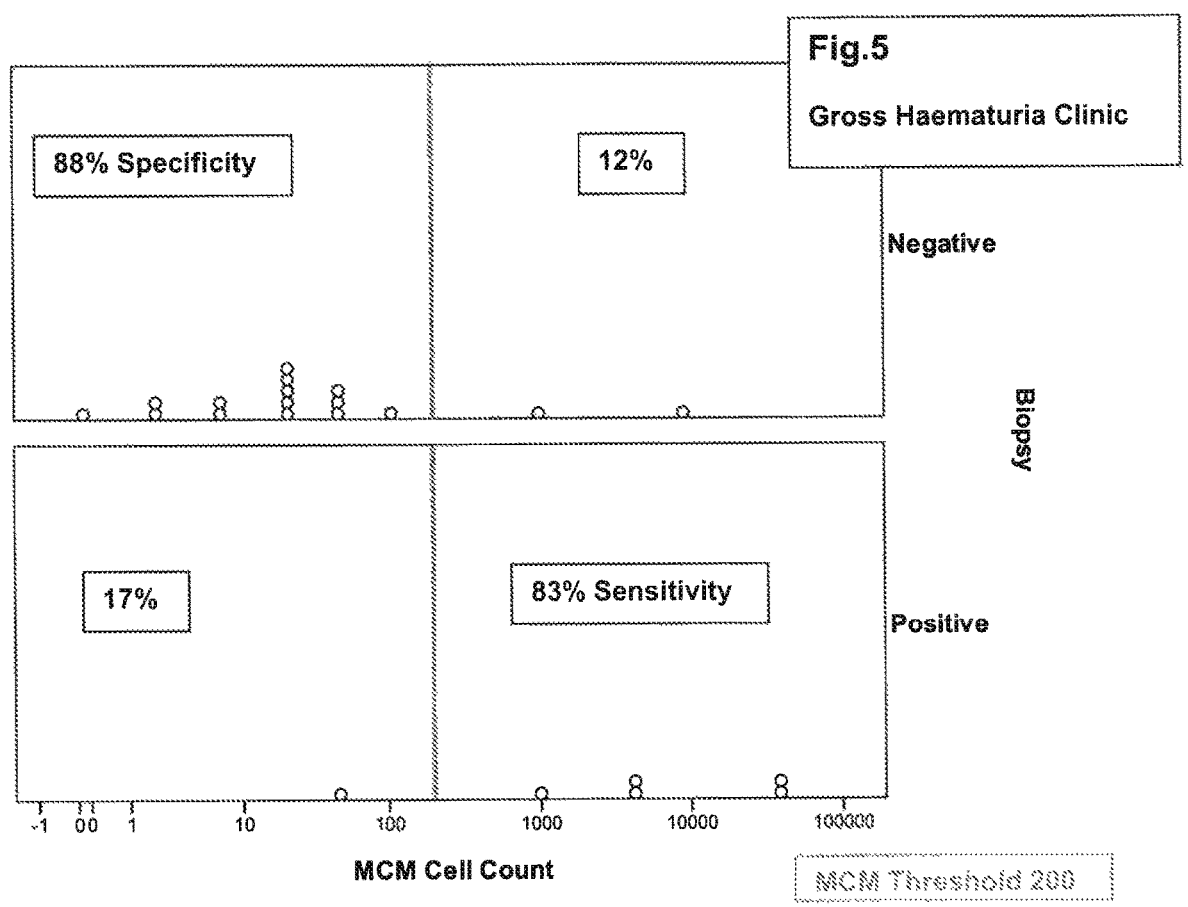

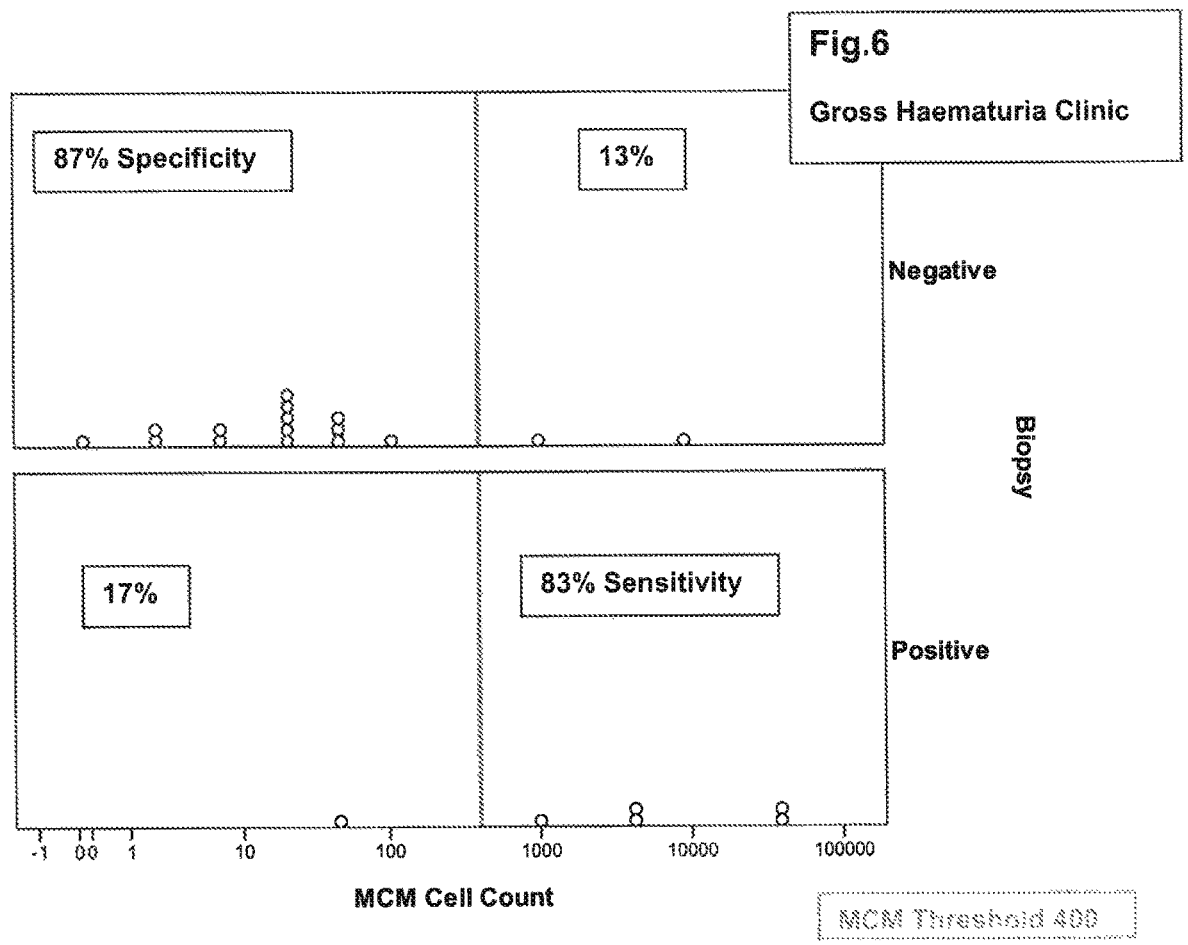

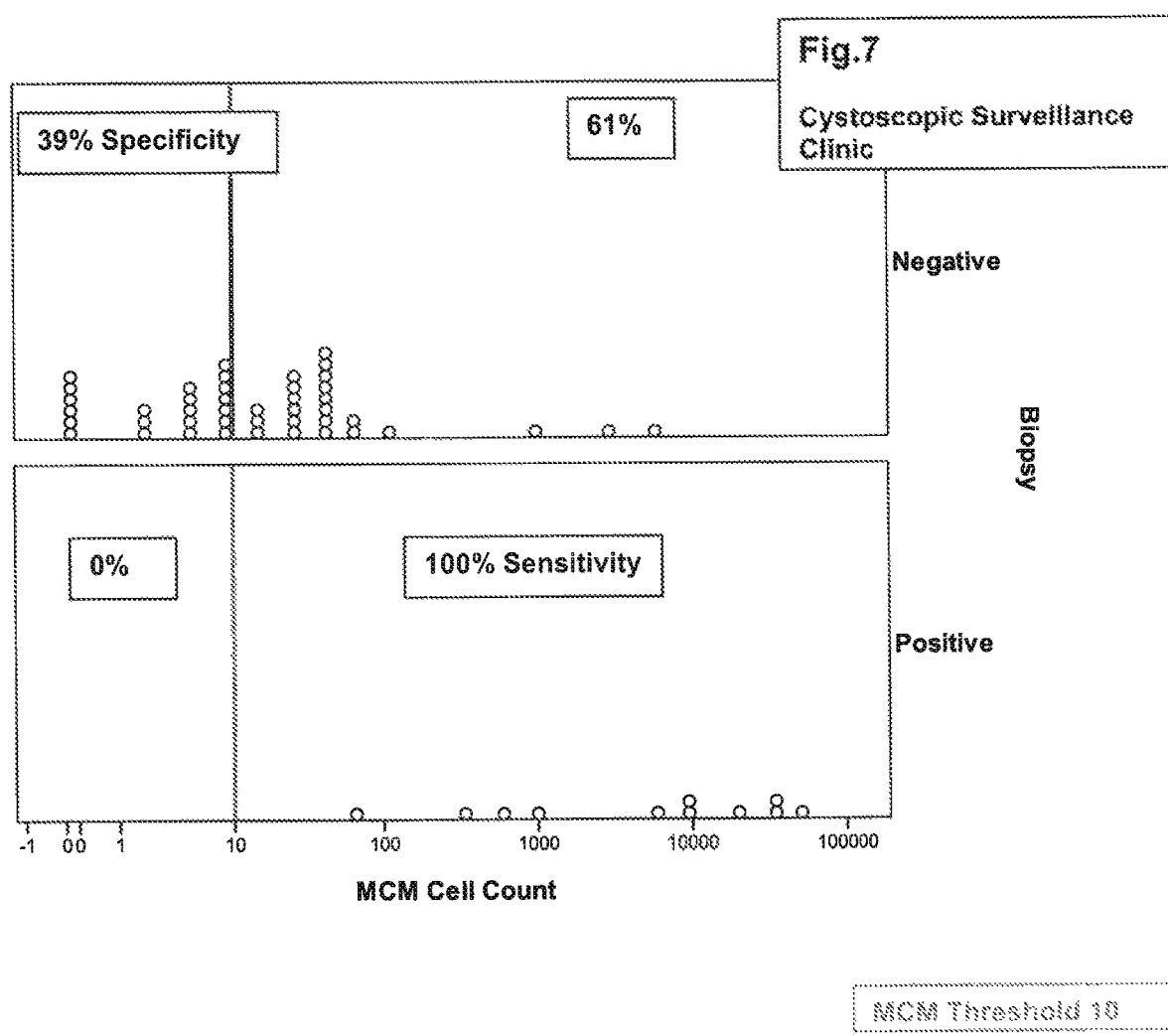

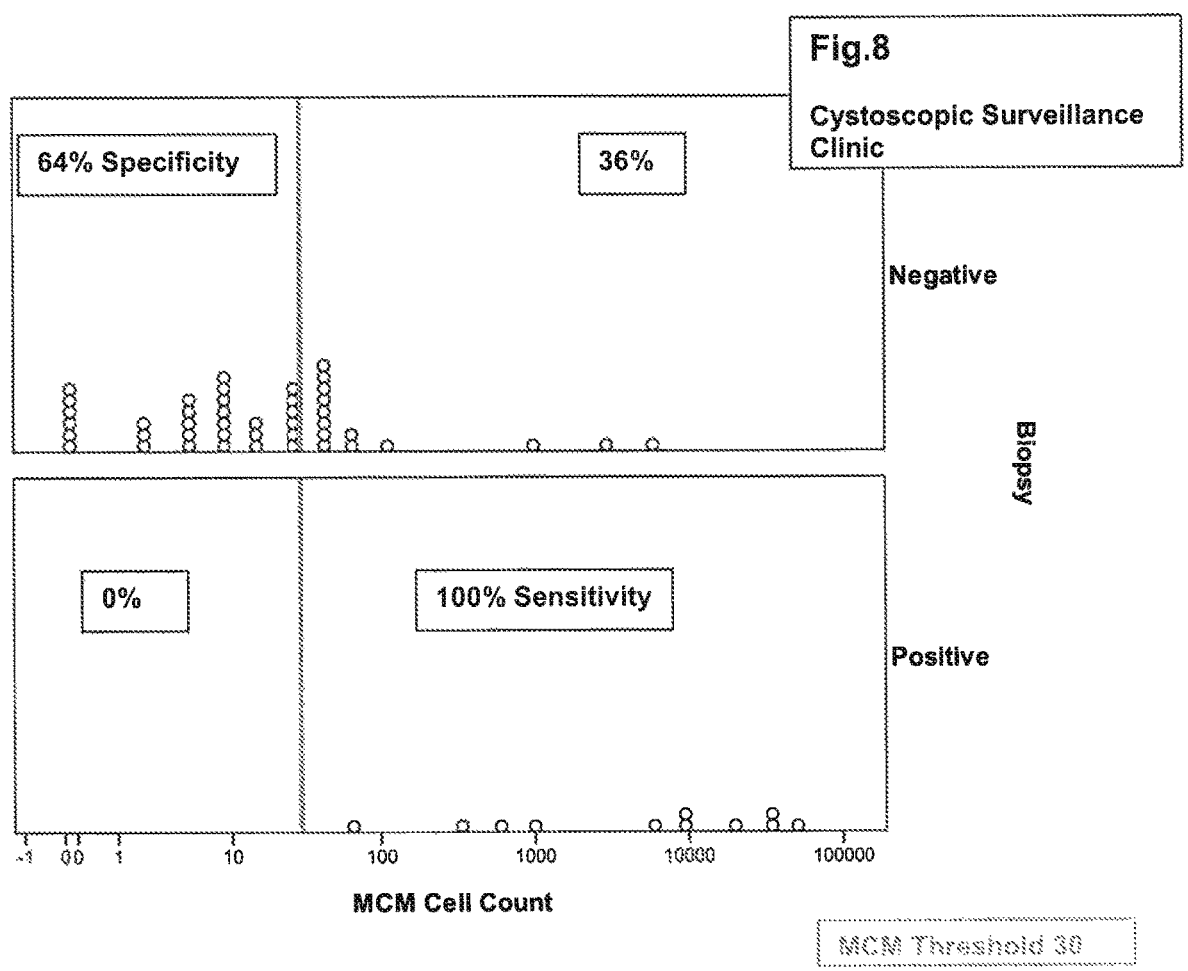

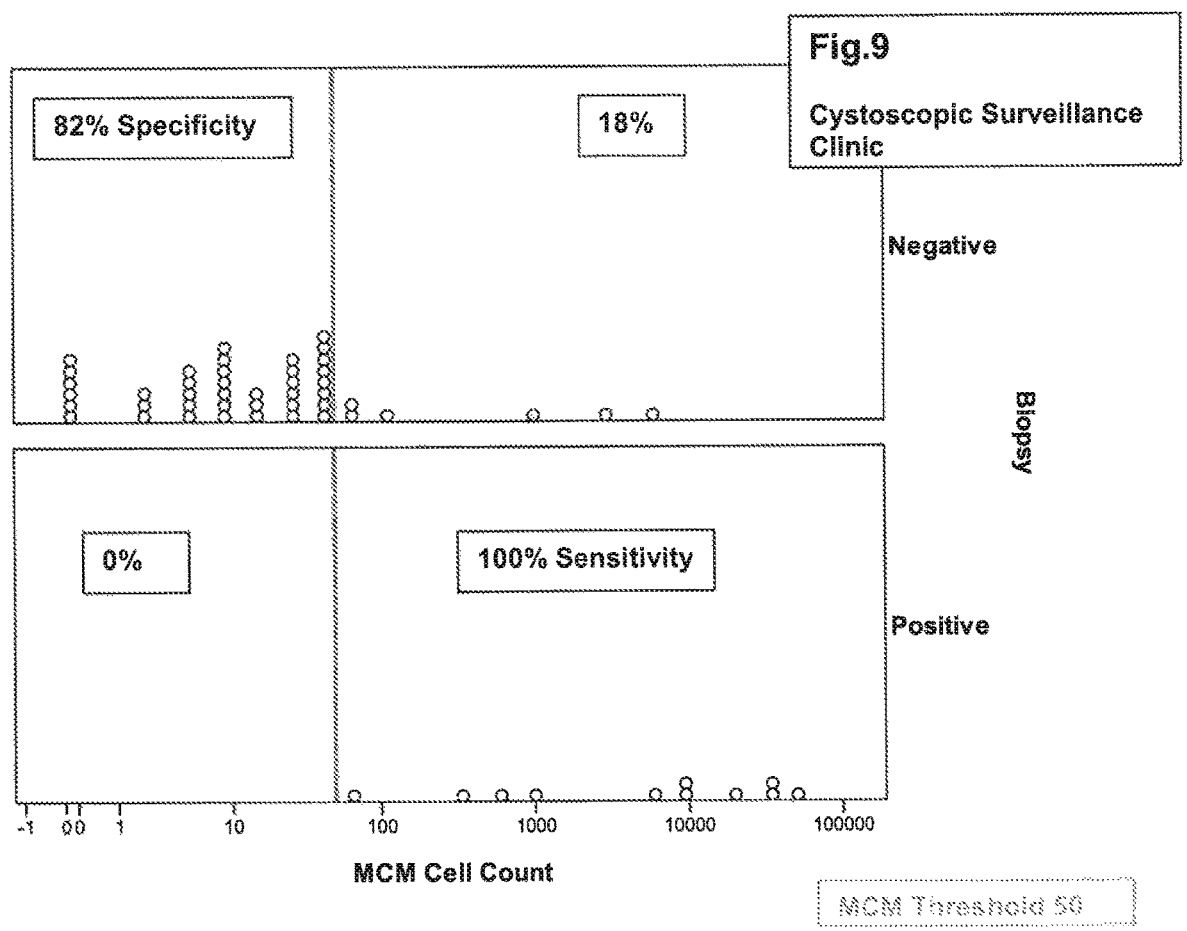

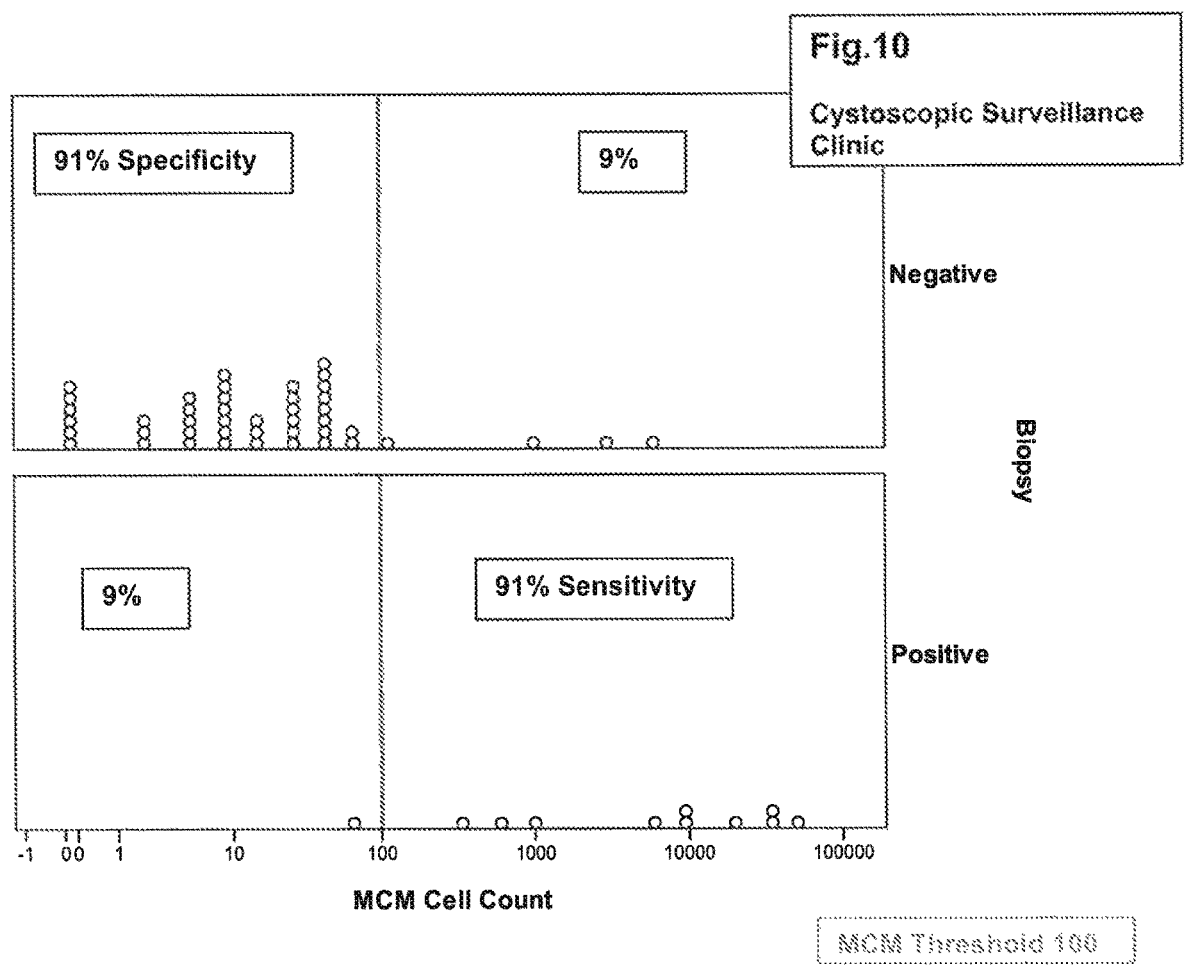

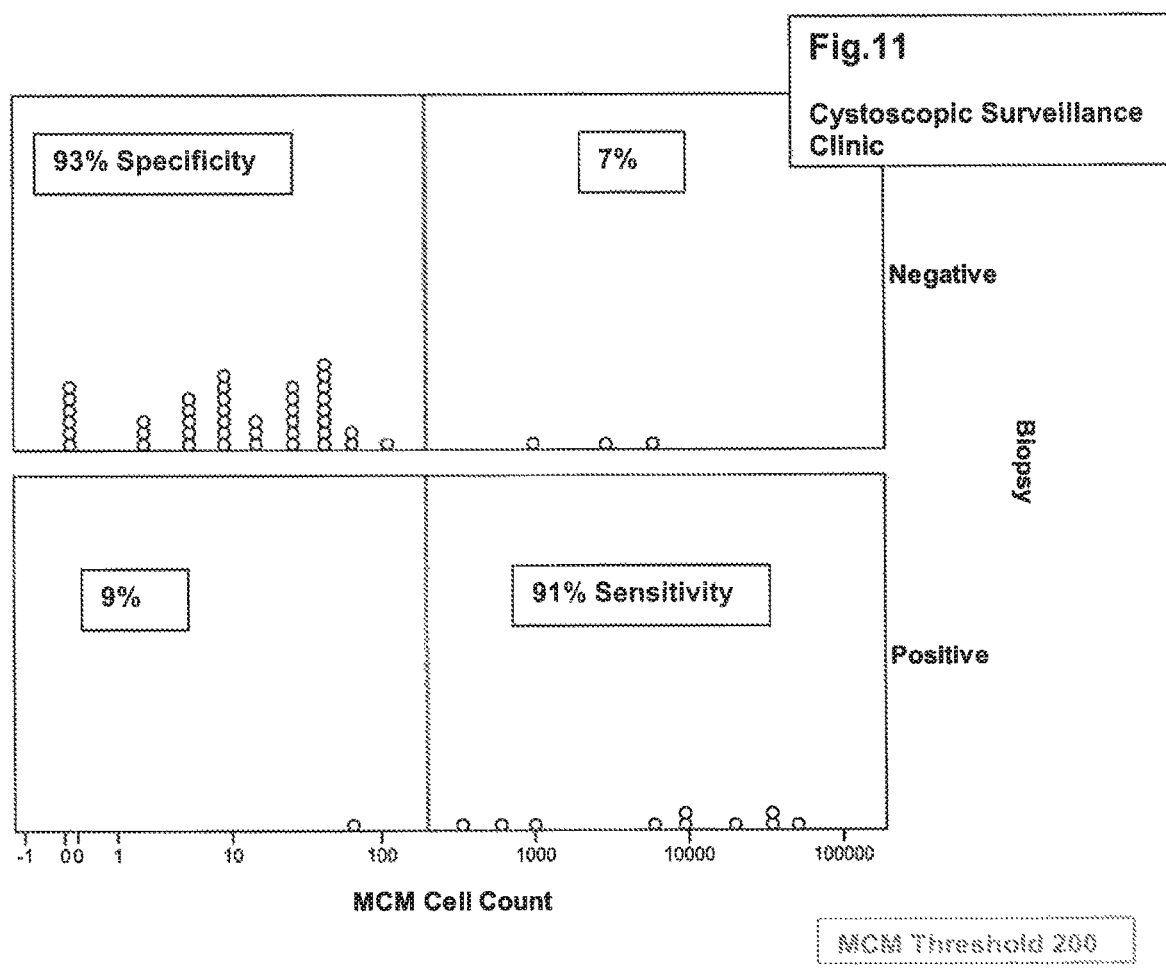

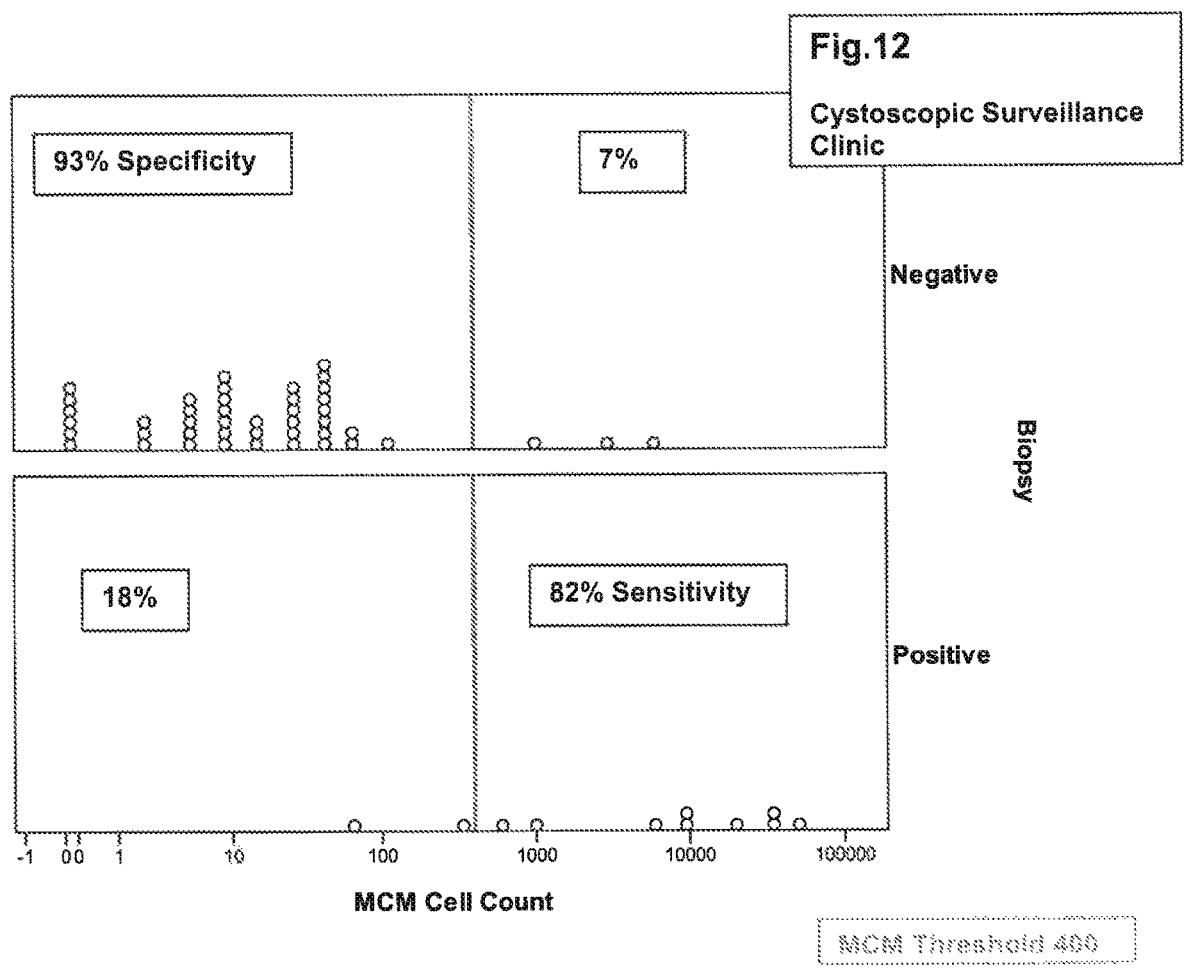

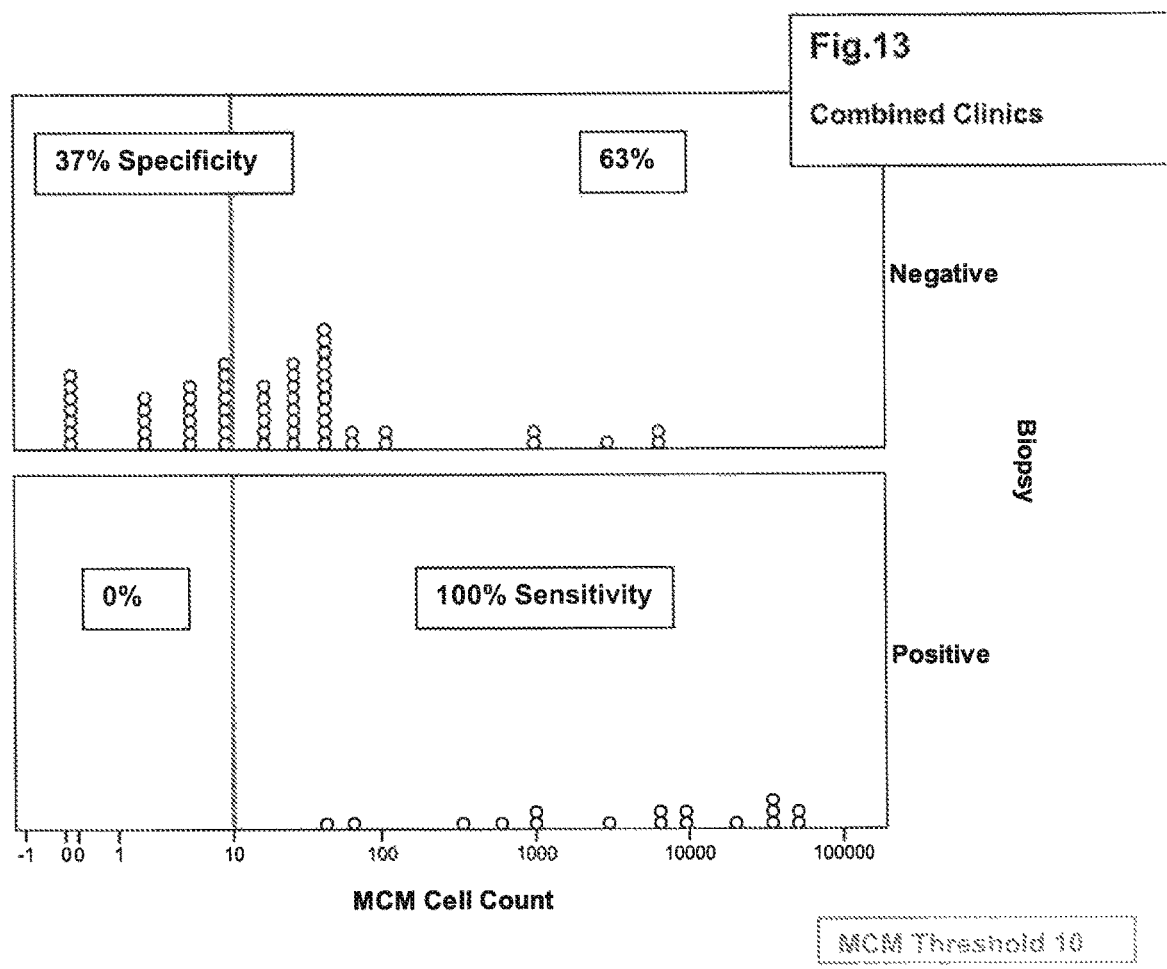

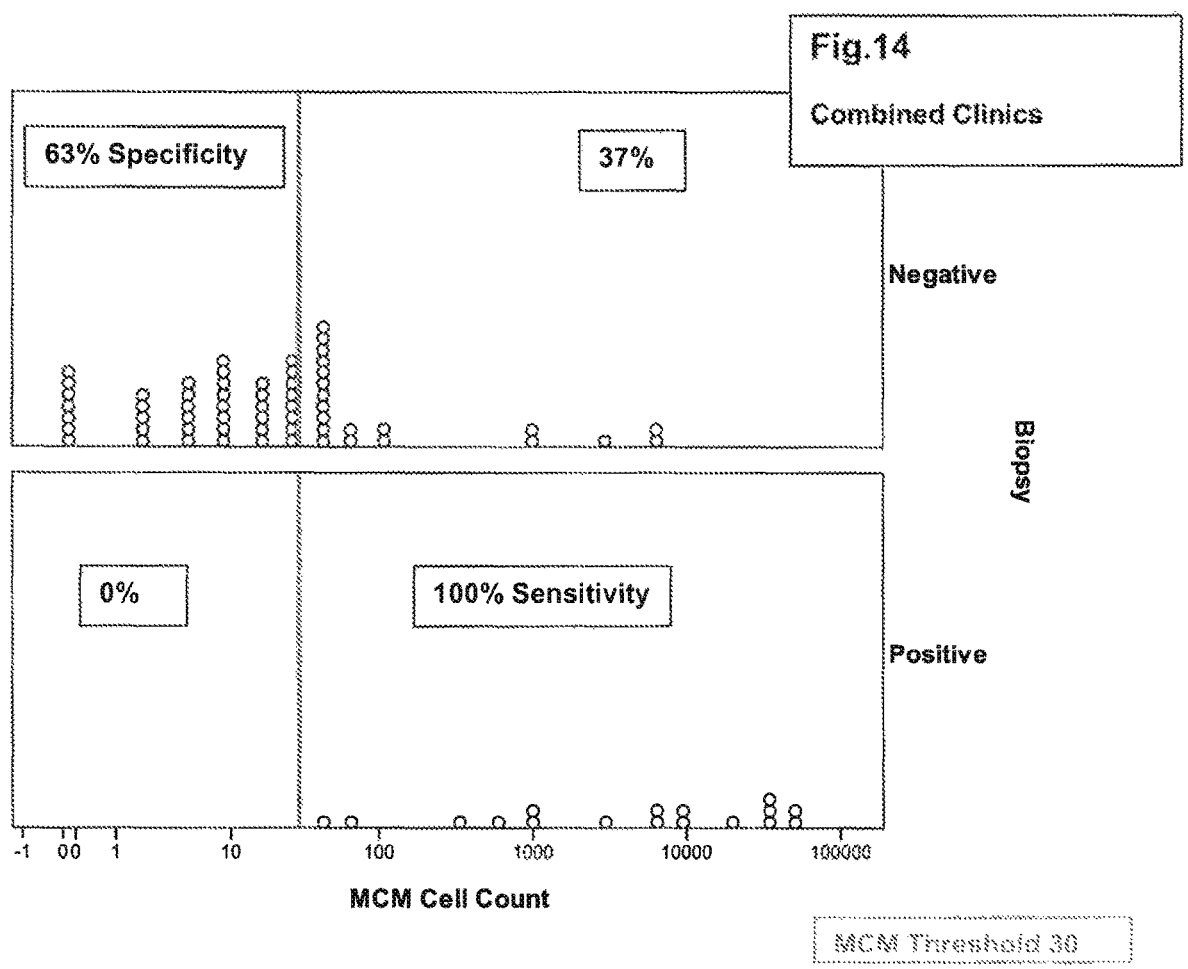

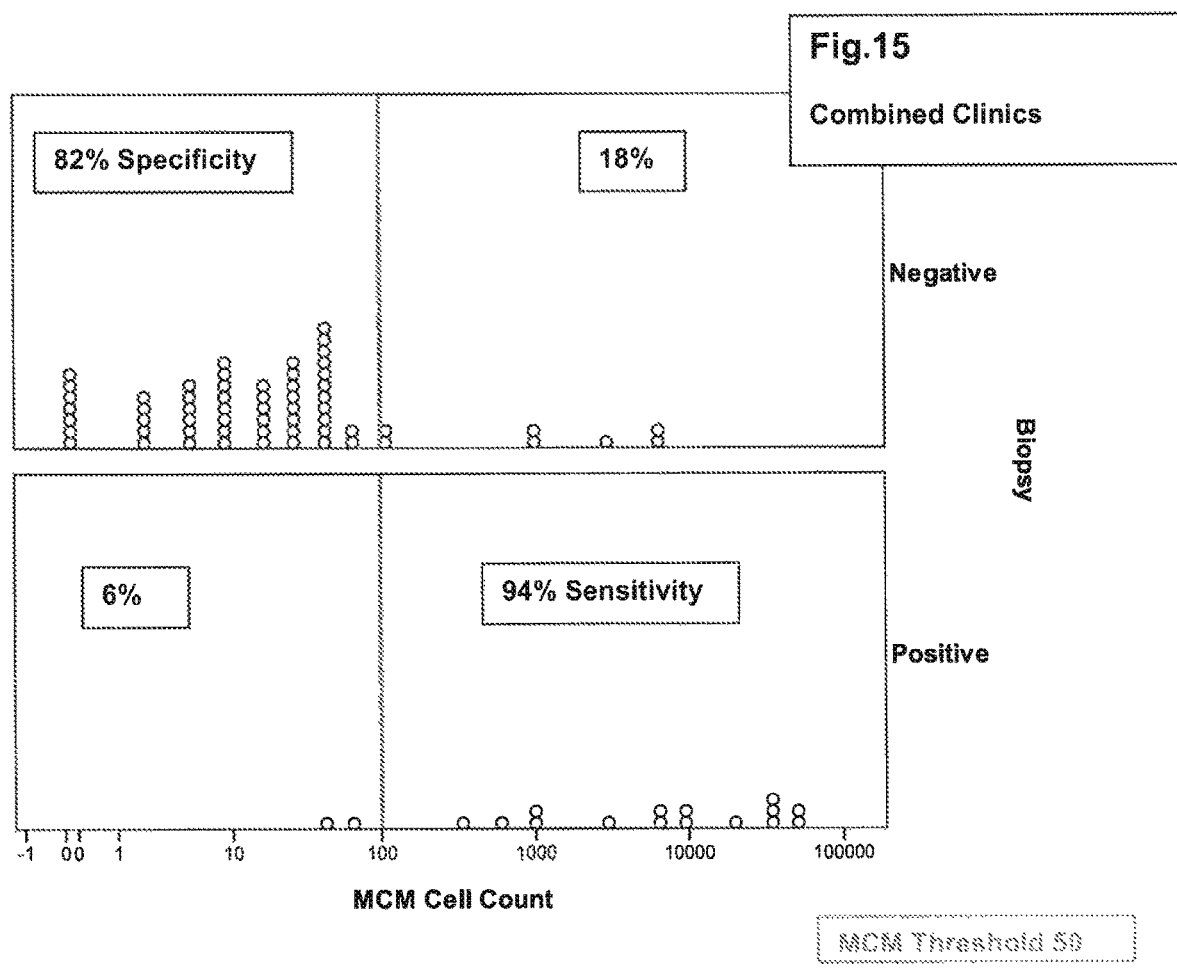

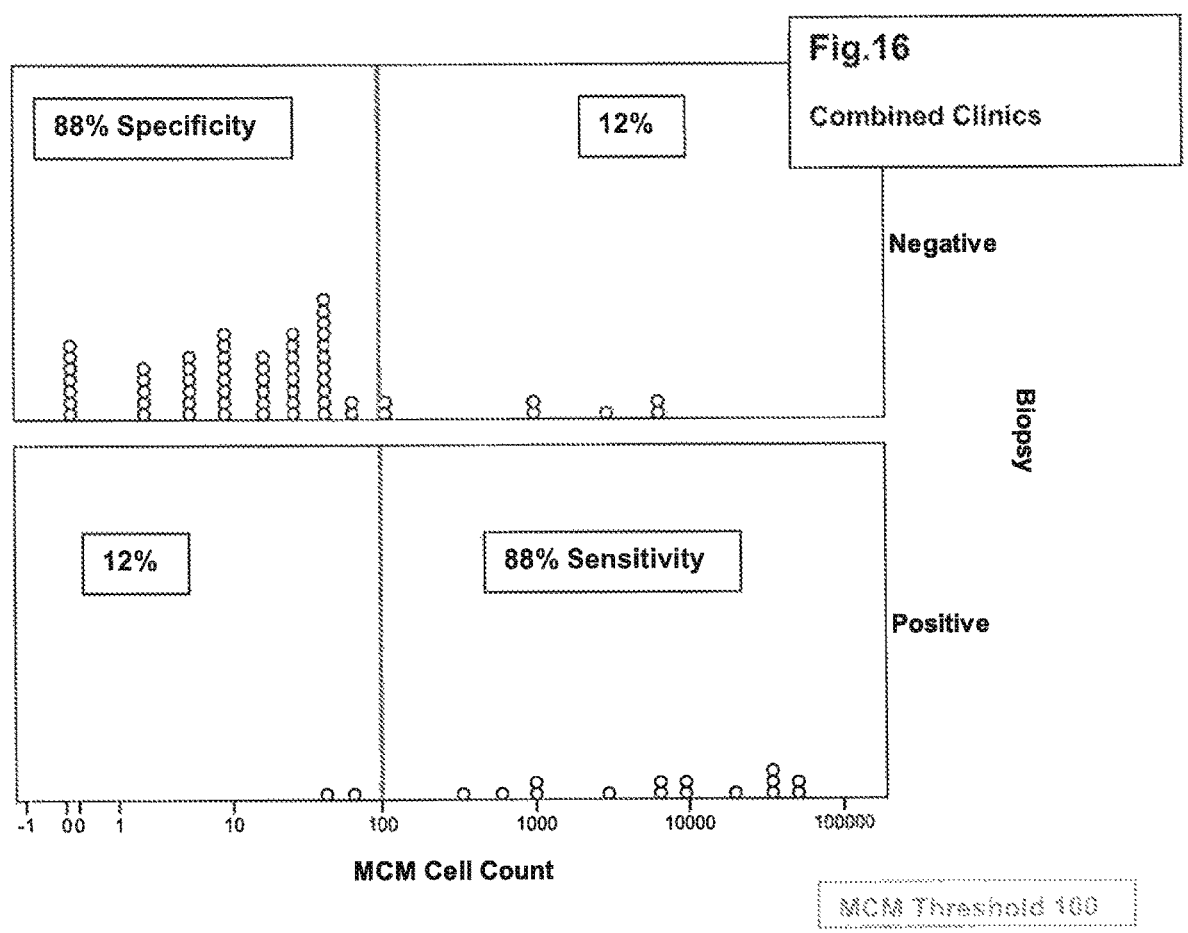

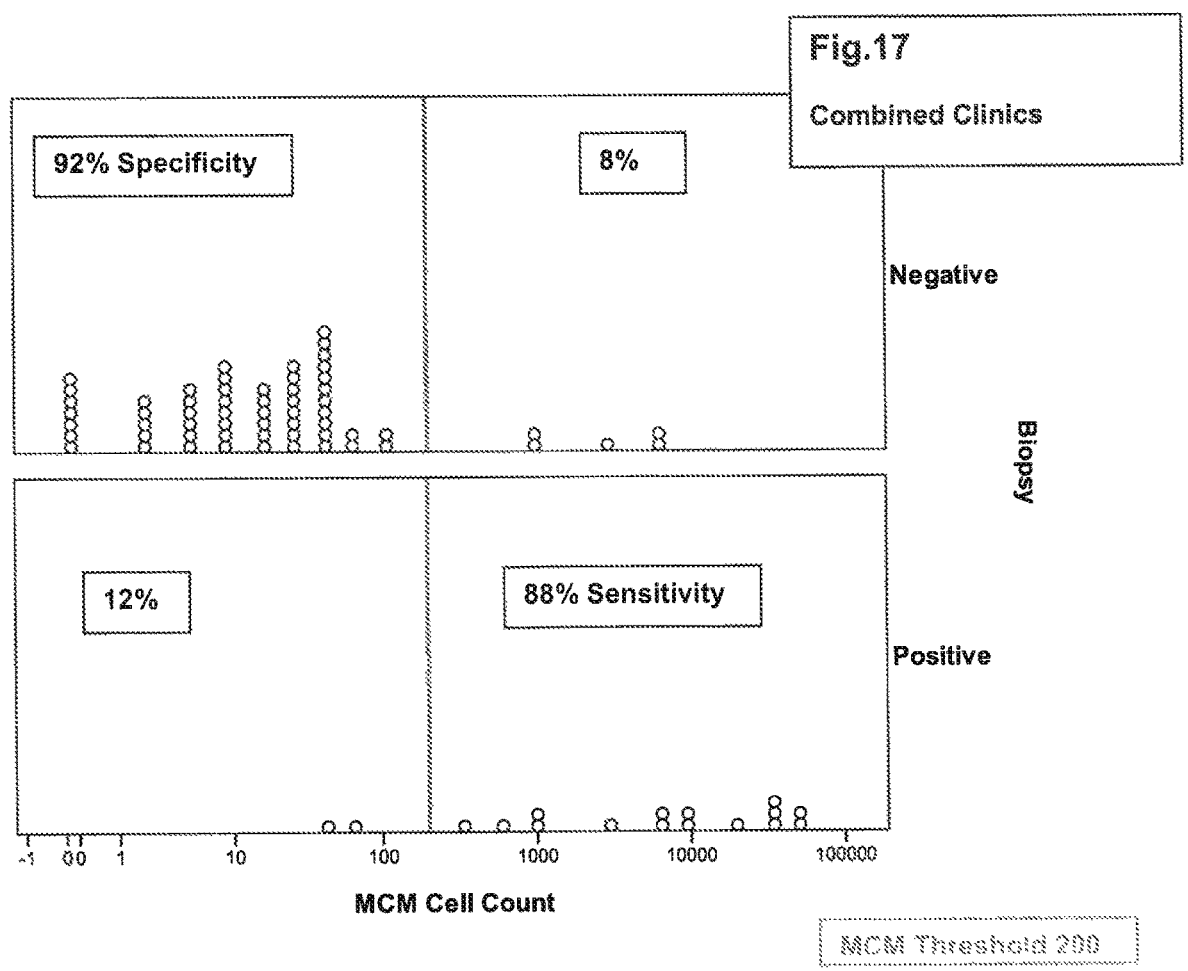

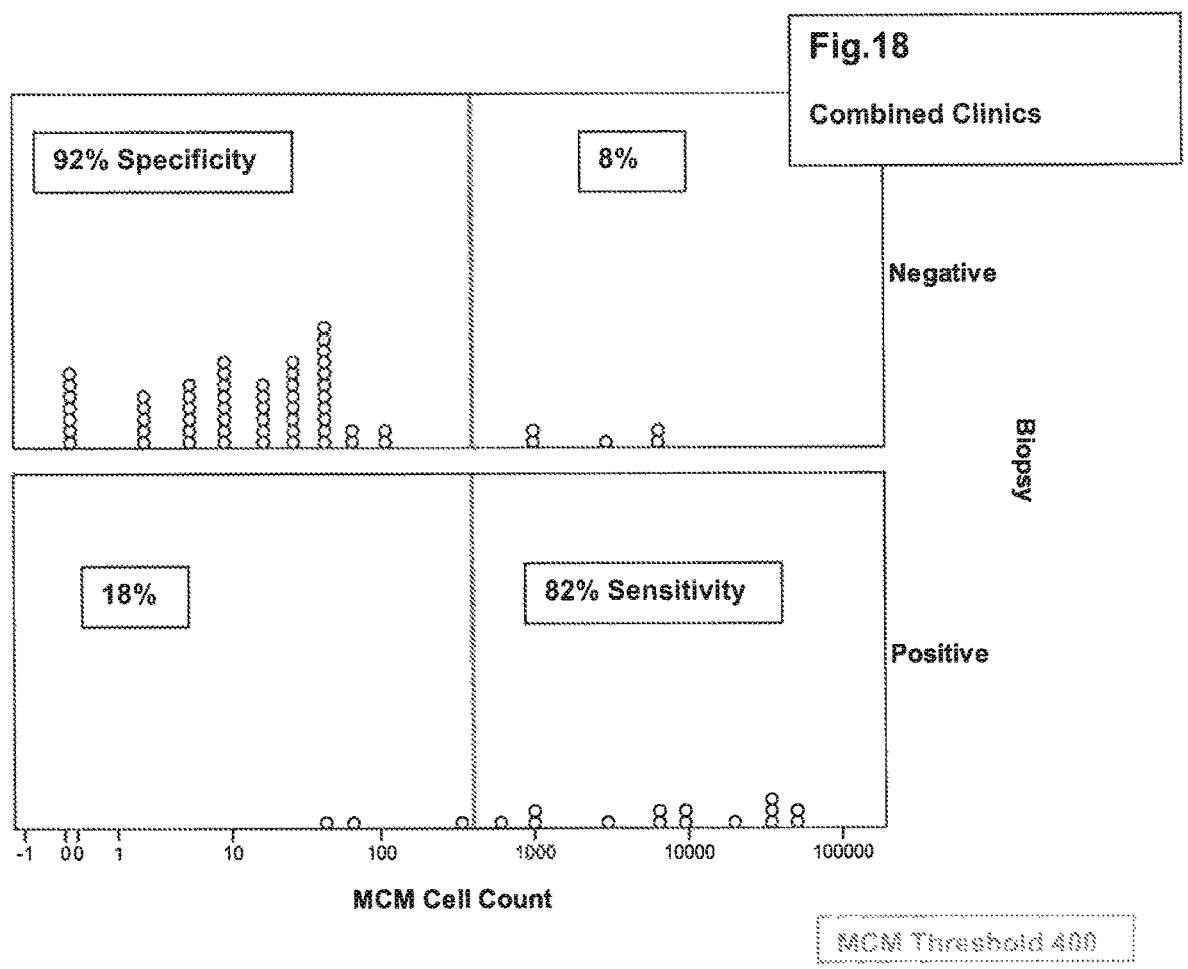

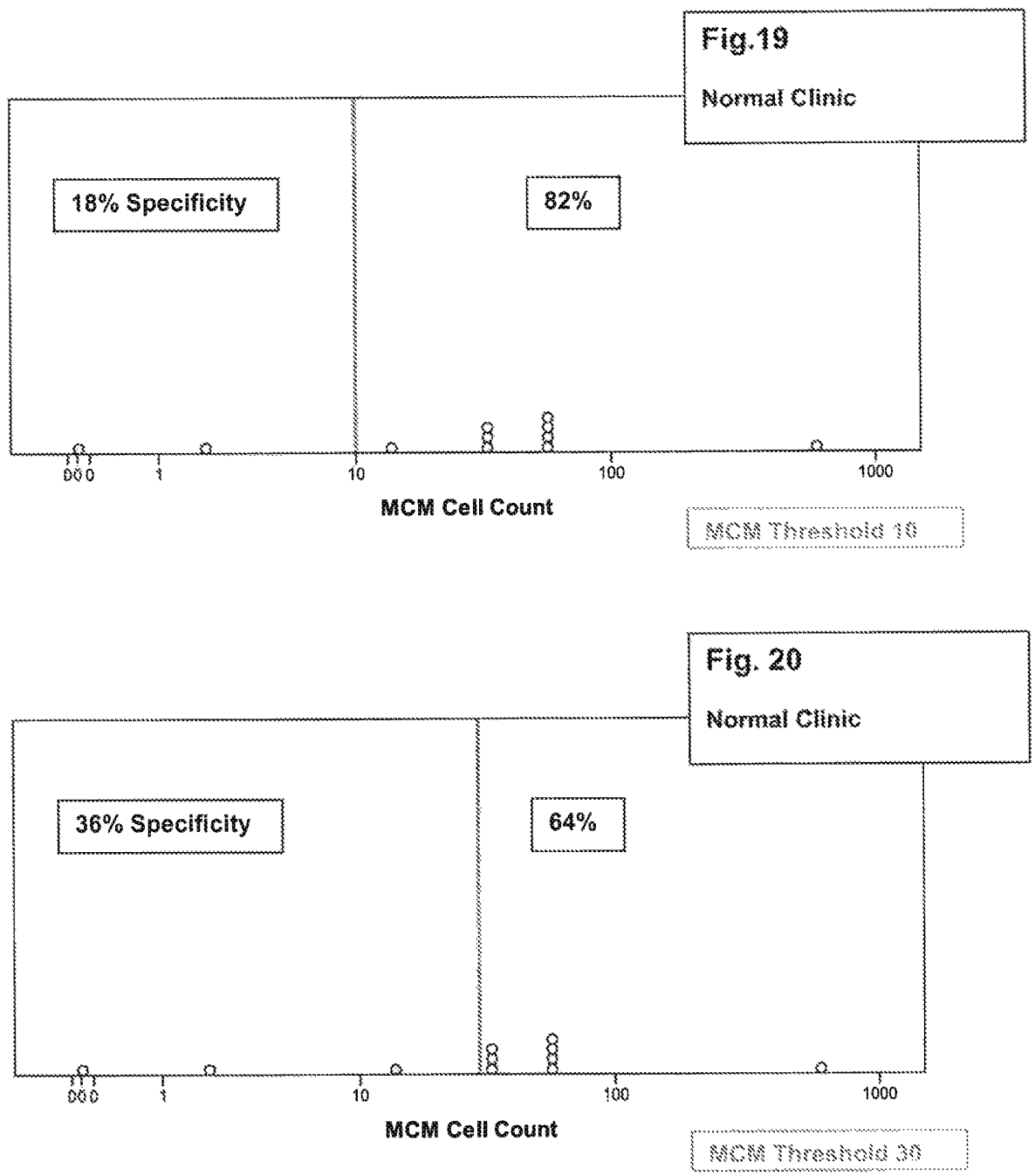

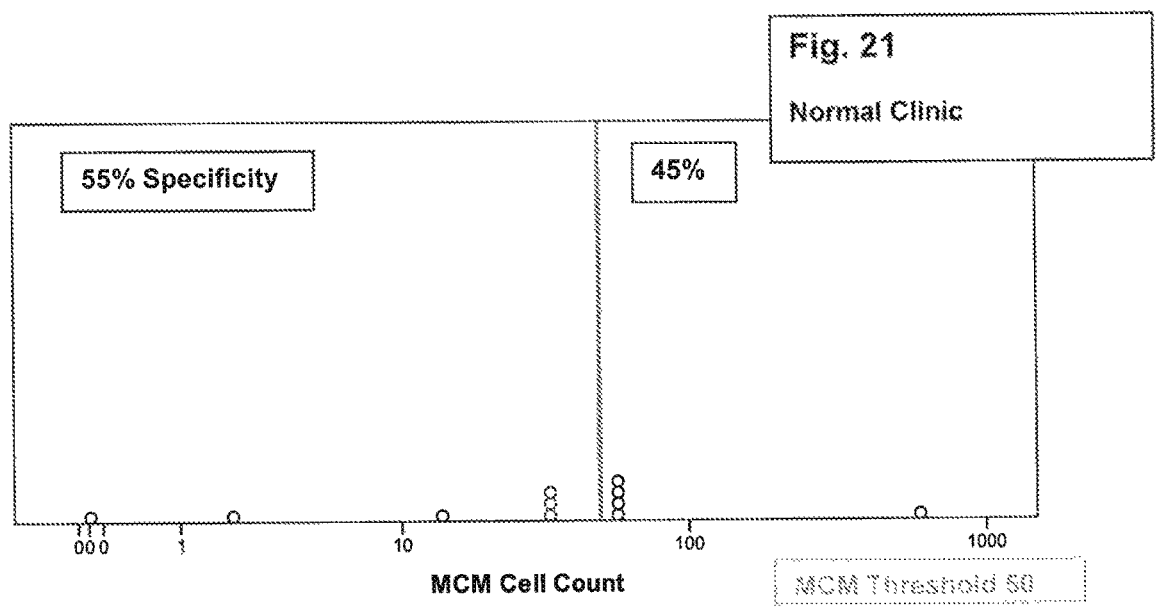
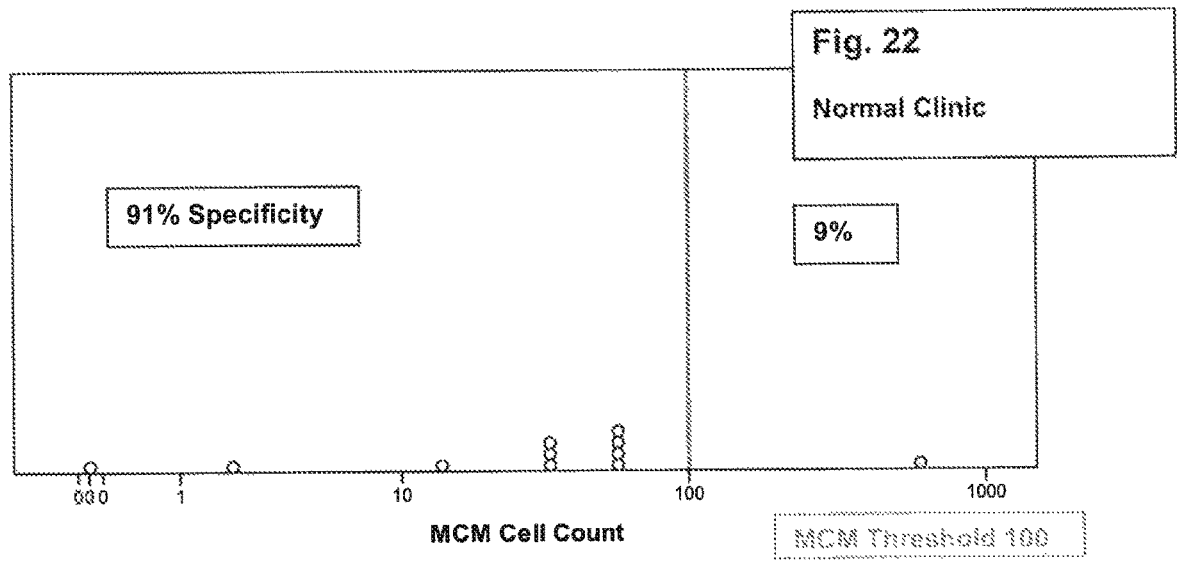

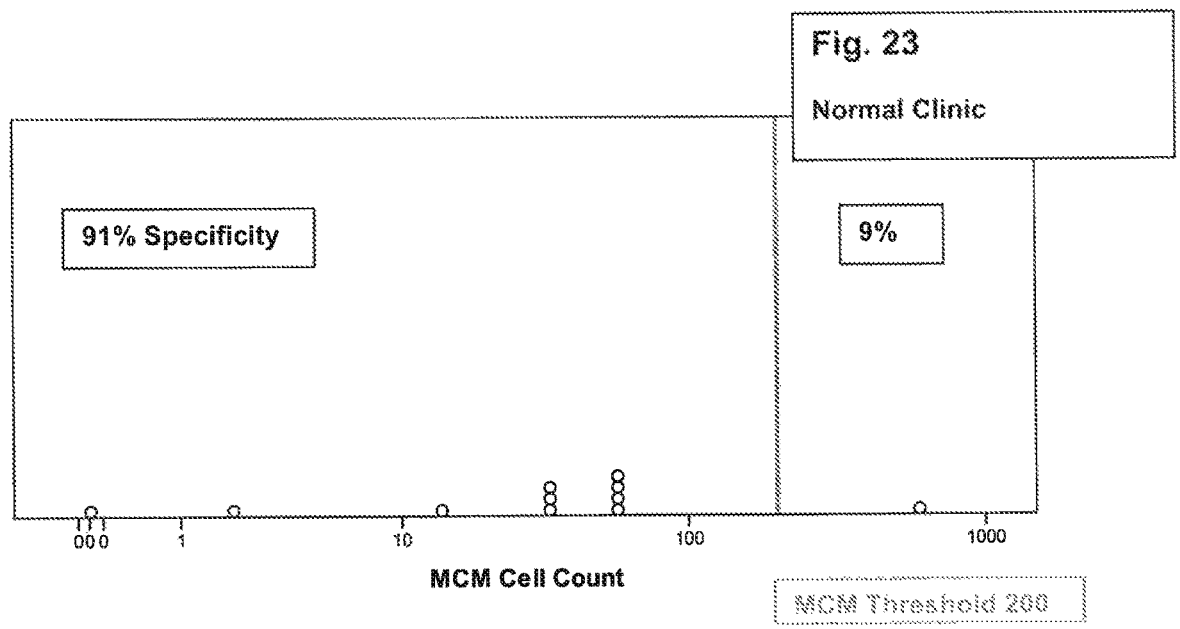
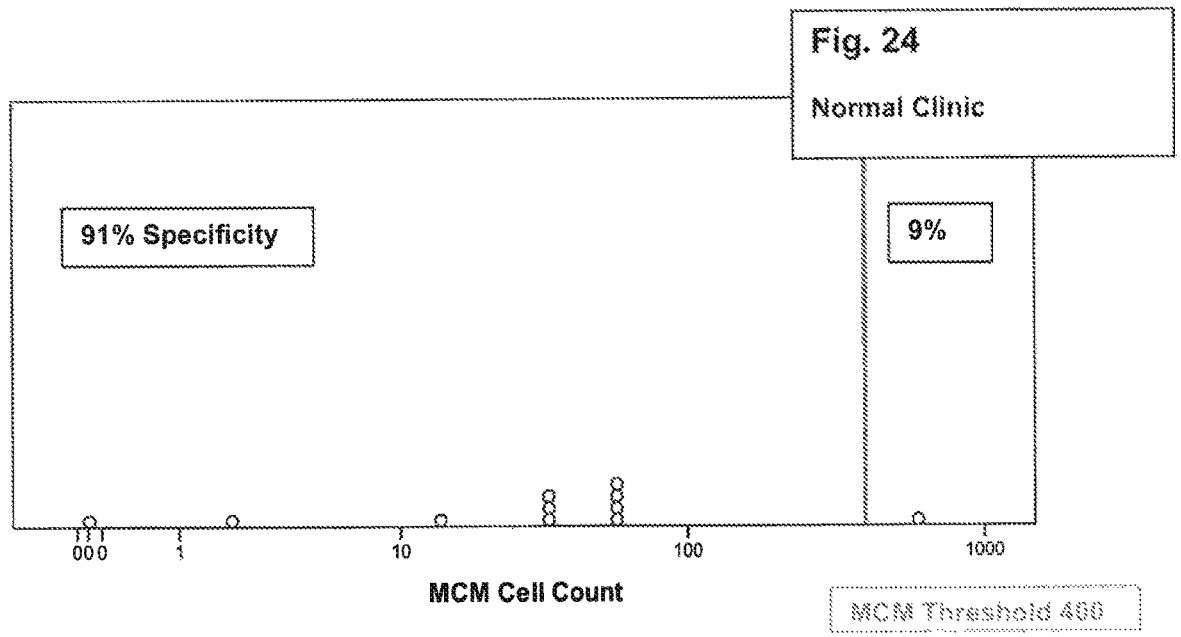

PATIENTS WITH MICROSCOPIC HAEMATURIA
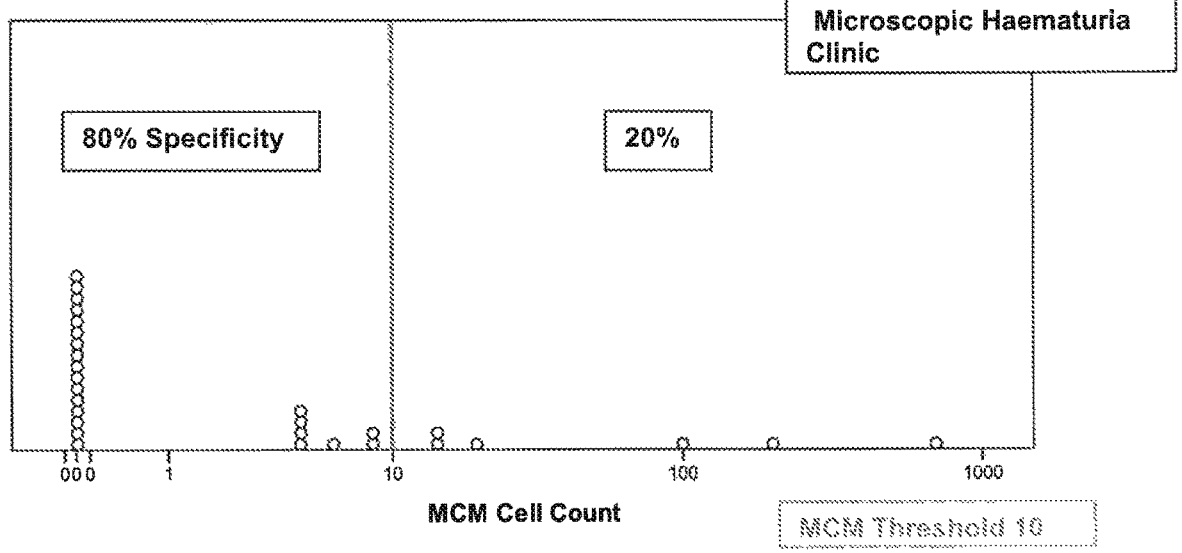
Fig. 25 Microscopic Haematuria Clinic
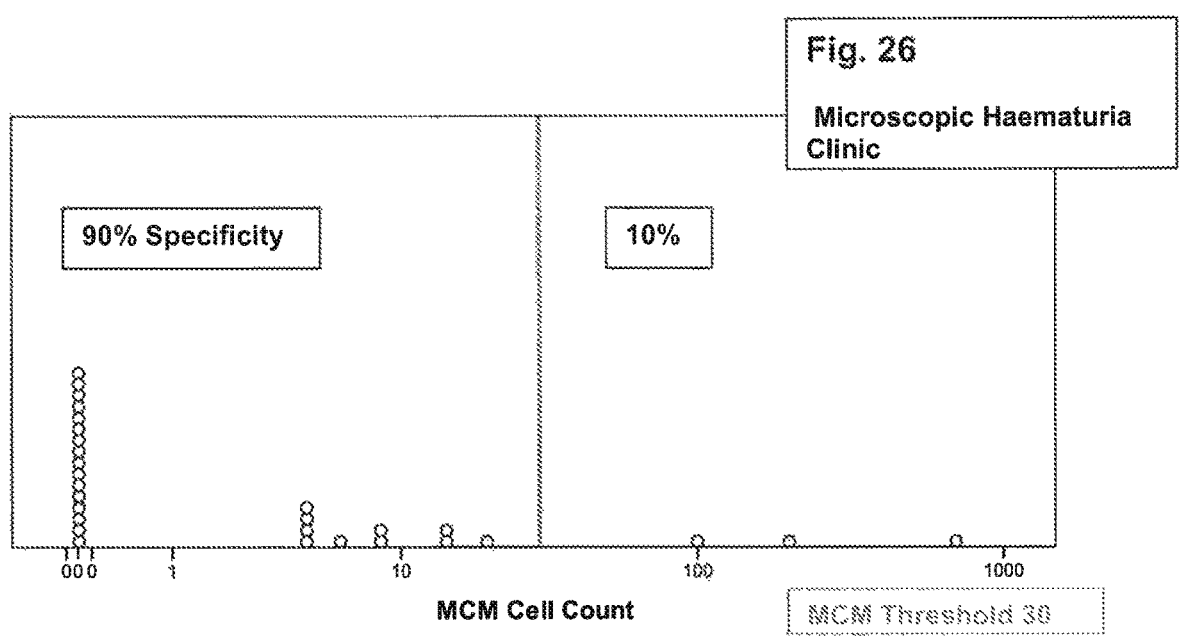
Fig. 26 Microscopic Haematuria Clinic

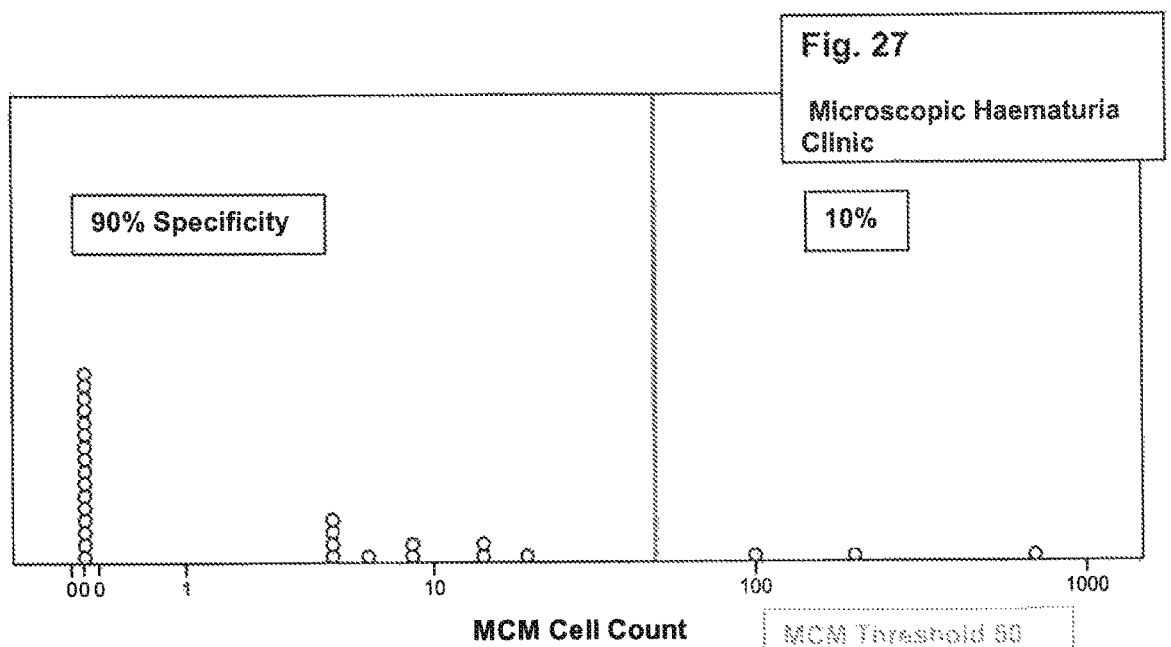
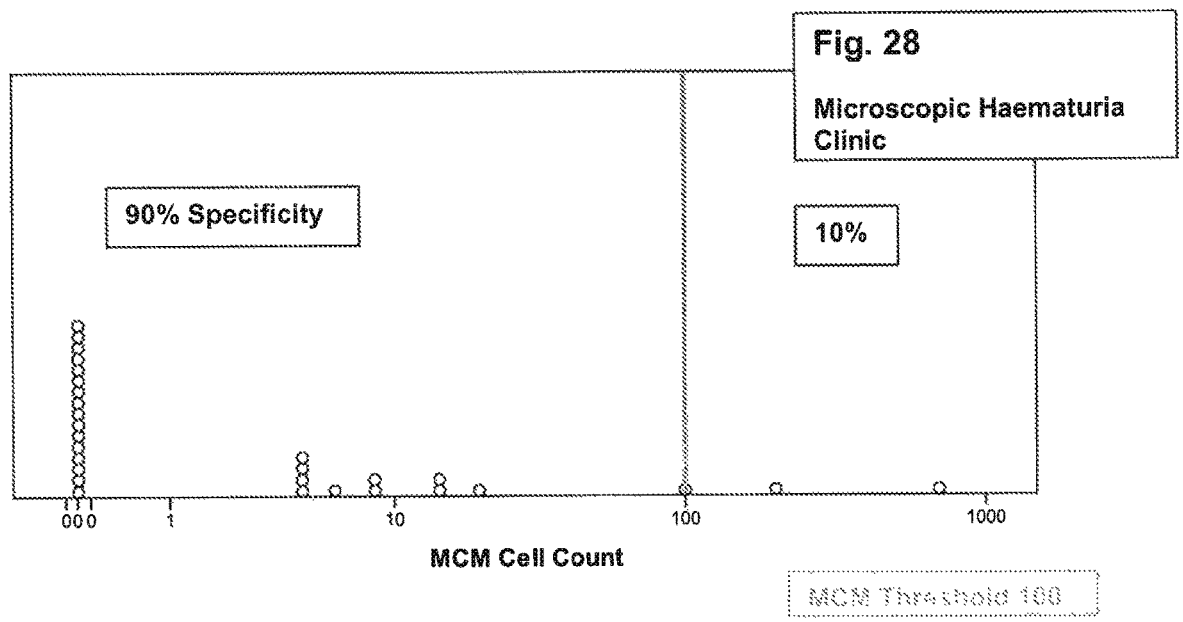

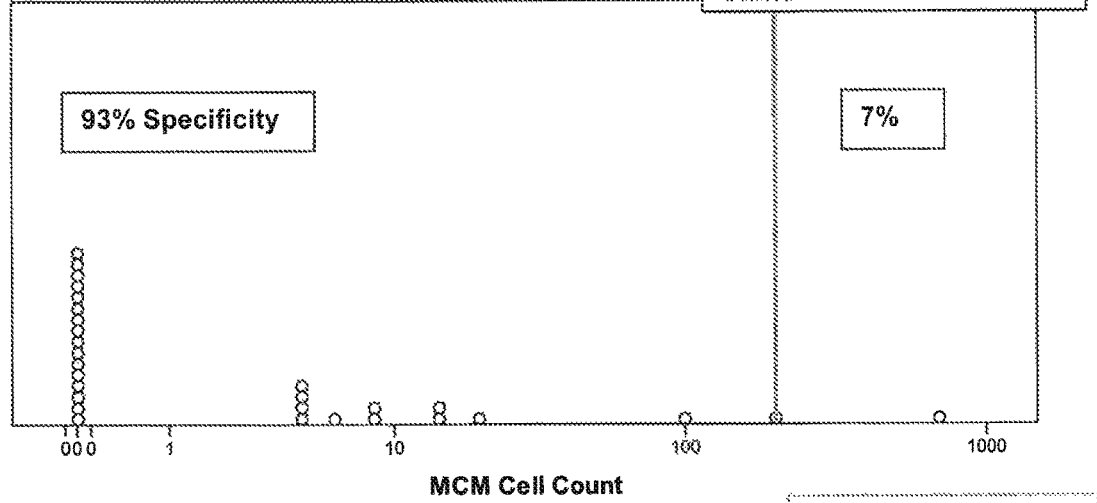
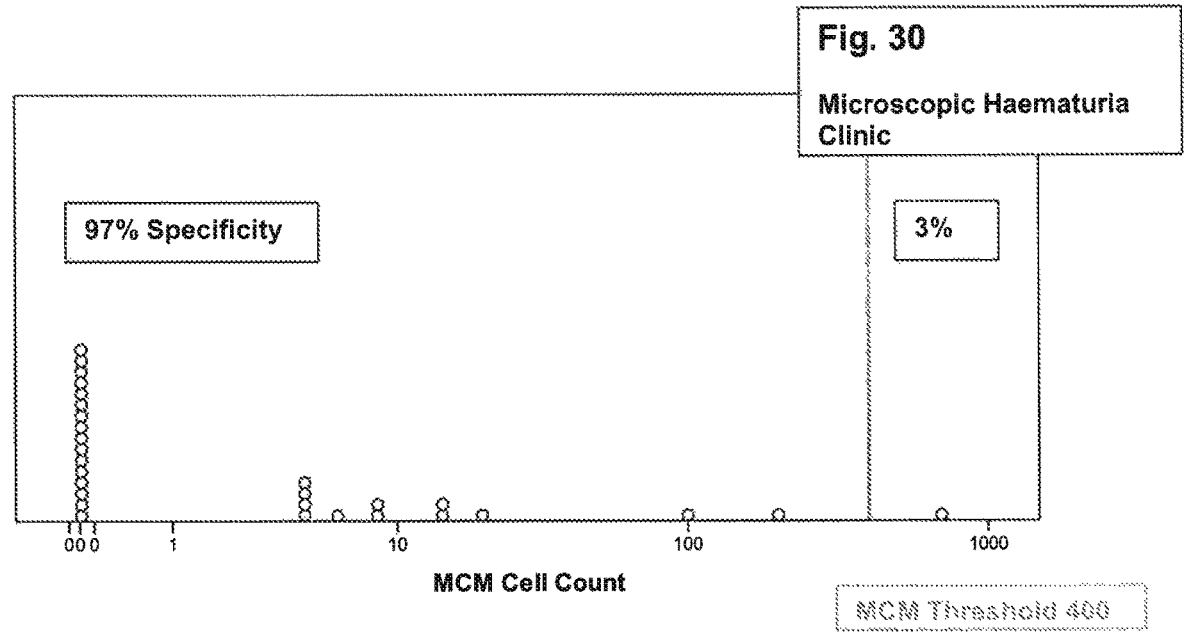

DIAGNOSTIC METHOD

This application is a Continuation claiming priority to and benefit of a prior application U.S. Ser. No. 13/512,585, Diagnostic Method, filed Nov. 21, 2012, which is a section 371 U.S. National phase Application from PCT/GB12/00008, filed Jan. 6, 2012, which claims priority to UK 1100223.5, filed Jan. 7, 2011. Applicants claim priority through these prior applications. The full disclosure of the prior applications is incorporated herein by reference.

FIELD OF THE INVENTION

The invention relates to a screening method for bladder cancer.

BACKGROUND TO THE INVENTION

Bladder cancer is a common disease with an estimated 1 million cases diagnosed worldwide each year. Incidence rates are highest in industrialised countries where over 90% of bladder cancers are of transitional origin. Approximately 75% of patients initially diagnosed with transitional cell carcinoma present with superficial tumours that can be treated by transurethral resection. Clinical management of patients with transitional cell carcinoma is complicated because the recurrence rate of superficial disease is greater than 60% and about 40% of patients with superficial disease will have tumour recurrence within 5 years if treated by trans-urethral resection of tumour alone [Ozono et al., Jpn J Clin Oncol 2001; 31: 536-540]. Furthermore, up to 30% of recurrent bladder tumours will progress to invasive disease [Zieger et al., BJU Int 2000; 85: 824-828]. Thus, early detection and monitoring of patients having, or suspected of having, bladder cancer is important for successful treatment.

The current clinical gold standard for diagnosing bladder cancer involves cystoscopy either under local or general anaesthetic, followed by solid tissue biopsy where that is appropriate. Cystoscopy is routinely used to test patients who present with haematuria or irritative voiding, both symptoms of early transitional cell carcinoma that are more often related to less serious diseases such as urinary tract infection or benign prostatic hyperplasia. Patients with these nonspecific symptoms may undergo extensive urological investigation even though only a small percentage of them actually have malignancies. Because cystoscopy is invasive and costly, both patients and clinicians would greatly benefit from the development of cost-effective and non-invasive tools for the diagnosis and surveillance of bladder cancer. There is, therefore, an urgent need for a reliable, non-invasive screening tool for the diagnosis of bladder cancer.

Cytology analysis of voided urine is the most commonly used non-invasive method for detecting transitional cell carcinoma but its utility is constrained by its low sensitivity other than in cases of high grade malignancy (grade 2 or grade 3).

Previous studies have identified minichromosome maintenance proteins (MCM) as key regulators in the cell cycling process of epithelial tissue [Baldwin et al., Nature Reviews Cancer 2003; 3:217-26, Chatrath et al., British Journal of Cancer 2003 89:1048-54, Sirieix et al., Clinical Cancer Research 2003; 9:2560-6; Davies et al., Lancet 2002; 359: 1917-19; Freeman et al., Clinical Cancer Research 1999; 5: 2121-2132; Stoeber et al., Lancet 1999; 354: 1524-1525; Williams et al., Proc Natl Acad Sci USA 1998; 95: 14932-14937]. Multiple conserved mechanisms limit DNA replication to once per cell cycle. An essential role in proliferation for MCMs and their regulators makes them potentially important biomarkers for routine clinical use in cancer detection and prognosis.

The present invention is based on the finding that there is an association between the number of MCM positive cells in the urine of an individual and their risk of having or developing bladder cancer. Specifically the present inventors have demonstrated that there is a normal range for the number of MCM positive cells one would expect to find in the urine of a healthy individual and patients having a number of positive cells above this normal range are at a significantly increased risk of having, or going on to develop, bladder cancer. In addition the present inventors have extended this finding to patients who have already had cancer and are at an increased risk of relapse.

Statements of Invention

According to a first aspect of the invention there is provided a method of detecting a subject suffering from, or at risk of suffering from, bladder cancer the method comprising
  i) providing a body fluid sample isolated from a subject;
  ii) isolating cells from said sample to provide a cell sample;
  iii) contacting the sample with a specific binding member capable of binding to a minichromosome maintenance (MCM) polypeptide(s);
  iv) determining the binding of said specific binding member to the cell sample;
  v) counting those cells in said cell sample which bound to said specific binding member to provide a cell count;
  vi) determining, based on the cell count, whether the subject has, or is at risk of having, bladder cancer.

Preferably said determining step (vi) is based upon a measurement of MCM bound/labelled cells relative to a threshold number, wherein said measurement above or equal to said threshold is indicative of bladder cancer or a risk of bladder cancer.

The threshold number may be at least about 10 cells, for example the threshold number may be at least about 10 cells but less than about 400 cells. For example, the threshold number may be at least 30 cells for example at least 40 or 50 cells. The threshold number may be at least 100 cells for example at least 200 cells. As used herein, the term "about" refers to an understood variation from the stated value. It is to be understood that such a variation is always included in any given value provided herein, whether or not it is specifically referred to. Examples of such a variation include + or −10.

The subject may be presenting with symptoms which may be associated with bladder cancer including haematuria or lower urinary tract symptoms (for example frequent voiding, dysuria, urgency of micturition, or nocturia). Thus the invention provides a method of detecting bladder cancer in a subject presenting with symptoms associated with bladder cancer, for example haematuria, the method comprising
  i) providing a body fluid sample isolated from a subject;
  ii) isolating cells from said sample to provide a cell sample;
  iii) contacting the sample with a specific binding member capable of binding to a minichromosome maintenance (MCM) polypeptide(s);
  iv) determining the binding of said specific binding member to the cell sample;

v) counting those cells in said cell sample which bound to said specific binding member to provide a cell count; and vi) determining, based on the cell count, whether the subject has, or is at risk of having, bladder cancer wherein said determining step (vi) is based upon a measurement of MCM bound cells relative to a threshold number, wherein said measurement above or equal to said threshold is indicative of bladder cancer or a risk of bladder cancer. The threshold number may be at least about 10 cells, for example about 30 or 50 cells. Preferably the threshold number is at least about 50 cells, for example between about 50 and 400 cells, such as about 50 to 200, or 50 to 100, cells. Preferably still the threshold number is about 50 cells.

In one embodiment, the invention provides a method of detecting bladder cancer in a subject presenting with gross haematuria (blood in urine), the method comprising i) providing a body fluid sample isolated from a subject;

ii) isolating cells from said sample to provide a cell sample;

iii) contacting the sample with a specific binding member capable of binding to a minichromosome maintenance (MCM) polypeptide(s);

iv) determining the binding of said specific binding member to the cell sample;

v) counting those cells in said cell sample which bound to said specific binding member to provide a cell count; and vi) determining, based on the cell count, whether the subject has, or is at risk of having, bladder cancer wherein said determining step (vi) is based upon a measurement of MCM bound cells relative to a threshold number, wherein said measurement above or equal to said threshold is indicative of bladder cancer or a risk of bladder cancer. The threshold number may be at least about 10 cells, for example about 30 or 50 cells. Preferably the threshold number is at least about 50 cells, for example between about 50 and 200, or 50 and 100, cells. Preferably still the threshold number is about 50 cells.

In a further embodiment, the invention provides a method of detecting bladder cancer in a subject presenting with symptoms which may be associated with bladder cancer including lower urinary tract symptoms (for example frequent voiding, dysuria, urgency of micturition, or nocturia) and/or micro haematuria, the method comprising i) providing a body fluid sample isolated from a subject;

ii) isolating cells from said sample to provide a cell sample;

iii) contacting the sample with a specific binding member capable of binding to a minichromosome maintenance (MCM) polypeptide(s);

iv) determining the binding of said specific binding member to the cell sample;

v) counting those cells in said cell sample which bound to said specific binding member to provide a cell count; and vi) determining, based on the cell count, whether the subject has, or is at risk of having, bladder cancer wherein said determining step (vi) is based upon a measurement of MCM bound cells relative to a threshold number, wherein said measurement above or equal to said threshold is indicative of bladder cancer or a risk of bladder cancer. The threshold number may be at least about 10 cells, for example about 30 or 50 cells. Preferably the threshold number is at least about 30 cells, for example between about 50 and 400 cells, such as about 50 to 200, or 50 to 100, cells. Preferably still the threshold number is about 30 cells. Typically, the subject is not presenting with gross haematuria.

The subject may have previous evidence of biopsy positive bladder cancer and/or may have relapsed with a further recurrence of tumour, presenting with symptoms (and in particular haematuria) or following outpatient cystoscopy indicative of tumour recurrence. Thus the invention provides a method of detecting bladder cancer in a subject who has a previous occurrence of bladder cancer or has relapsed, the method comprising i) providing a body fluid sample isolated from a subject;

ii) isolating cells from said sample to provide a cell sample;

iii) contacting the sample with a specific binding member capable of binding to a minichromosome maintenance (MCM) polypeptide(s);

iv) determining the binding of said specific binding member to the cell sample;

v) counting those cells in said cell sample which bound to said specific binding member to provide a cell count; and vi) determining, based on the cell count, whether the subject has, or is at risk of having, a recurrence of bladder cancer wherein said determining step is based upon a measurement of MCM bound cells relative to a threshold number, wherein said measurement above or equal to said threshold is indicative of bladder cancer or a risk of bladder cancer. The threshold number may be at least about 10 cells. Preferably the threshold number is at least about 200 cells, for example between about 200 and 400 cells. Preferably still the threshold number is about 200 cells.

The subject may be presenting with symptoms which may be associated with bladder cancer including haematuria or may have previous evidence of biopsy positive bladder cancer. Thus the invention provides a method of detecting bladder cancer in a subject presenting with symptoms associated with bladder cancer, for example haematuria, or who has a previous occurrence of bladder cancer, the method comprising:

i) providing a body fluid sample isolated from a subject;

ii) isolating cells from said sample to provide a cell sample;

iii) contacting the sample with a specific binding member capable of binding to a minichromosome maintenance (MCM) polypeptide(s);

iv) determining the binding of said specific binding member to the cell sample;

v) counting those cells in said cell sample which bound to said specific binding member to provide a cell count; and vii) determining, based on the cell count, whether the subject has, or is at risk of having, bladder cancer or a recurrence of bladder cancer wherein said determining step (vi) is based upon a measurement of MCM bound cells relative to a threshold number, wherein said measurement above or equal to said threshold is indicative of bladder cancer or a risk of bladder cancer. The threshold number may be at least about 10 cells. Preferably the threshold number is at least about 50 cells, for example between about 50 and 400 cells, such as about 50 to 200, or 50 to 100, cells. Preferably still the threshold number is between about 50 and 100 cells, for example about 70-80 cells.

The subject may be presenting with no symptoms of bladder cancer. Thus the invention provides a method of detecting bladder cancer in a subject not presenting with symptoms of bladder cancer, the method comprising:
  i) providing a body fluid sample isolated from a subject;
  ii) isolating cells from said sample to provide a cell sample;
  iii) contacting the sample with a specific binding member capable of binding to a minichromosome maintenance (MCM) polypeptide(s);
  iv) determining the binding of said specific binding member to the cell sample;
  v) counting those cells in said cell sample which bound to said specific binding member to provide a cell count; and determining, based on the cell count, whether the subject has, or is at risk of having, bladder cancer wherein said determining step (vi) is based upon a measurement of MCM bound cells relative to a threshold number, wherein said measurement above or equal to said threshold is indicative of bladder cancer or a risk of bladder cancer. The threshold number may be at least about 10 cells, for example about 10 to 50. Preferably the threshold number is about 10 cells or less, for example 5 to 10 cells.

Typically the body fluid is not blood or cerebrospinal fluid. The body fluid may be urine or semen. Alternatively the body fluid may be faeces. Preferably the body fluid is urine.

Preferably the method of the invention is useful in detecting or determining the presence of bladder cancer cells in a sample of body fluid, such as urine, from a subject, preferably human.

Cells may be isolated from the body fluid sample by any means known to the skilled person. Typically the cells are isolated by either centrifugation or filtration of the body fluid sample. Preferably the cells are isolated by filtration of the body fluid sample. In a preferred method of the invention the sample is subject to antigen retrieval. Antigen retrieval is standard in the art (see Hiraiwa et al refer to Shin et al (1991) Lab. Invest. 64, 693-702 which provides an exemplary approach). Antigen retrieval conditions may include contacting the cell sample with pH7.8 EDTA buffer at 95° for 45 min in water bath or Microwave.

In a method of the invention the MCM is selected from the group consisting of MCM 2, 3, 4, 5, 6 and 7. The MCM may be a combination of two or more different MCMs, for example, two different MCMs selected from the group consisting of MCM 2, 3, 4, 5, 6 and 7. For example the MCM may include MCM2 and one other MCM selected from MCM 3, 4, 5, 6 and 7. By way of further example the MCM may include MCM5 and one other MCM selected from MCM 2, 3, 4, 6 and 7. In a preferred method of the invention, the MCM is selected from the group consisting of MCM 2, 5 and 7. In a further preferred method of the invention, the MCM is selected from the group consisting of MCM 2 and 7.

In a preferred method of the invention the MCM is MCM 2.

In an alternative method of the invention the MCM is MCM 7.

In a method of the invention the MCM may include MCM 2 and MCM 5. In a further method of the invention the MCM may include MCM 2 and MCM 7. In a yet further method of the invention the MCM may include MCM 5 and MCM 7.

As used herein, a "specific binding member" is a member of a pair of molecules which have binding specificity for one another. The members of a specific binding pair may be naturally derived or wholly or partially synthetically produced. One member of the pair of molecules has an area on its surface, which may be a protrusion or cavity, which specifically binds to and is therefore complementary to a particular spatial and polar organisation of the other member of the pair of molecules. Thus, the members of the pair have the property of binding specifically to each other.

Examples of types of specific binding pairs are antigen-antibody, biotin-avidin, hormone-hormone receptor, receptor-ligand, enzyme-substrate, DNA-DNA (e.g. oligonucleotide). The present invention is generally concerned with antigen-antibody type reactions, although it also concerns small molecules which bind to the antigen defined herein.

The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term also covers any polypeptide or protein having a binding domain which is, or is homologous to, an antibody binding domain.

These can be derived from natural sources, or they may be partly or wholly synthetically produced. Examples of antibodies are the immunoglobulin isotypes (e.g., IgG, IgE, IgM, IgD and IgA) and their isotypic subclasses; fragments which comprise an antigen binding domain such as Fab, scFv, Fv, dAb, Fd; and diabodies. Antibodies may be polyclonal or monoclonal.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, humanised antibodies, including any polypeptide comprising an immunoglobulin binding domain, whether natural or wholly or partially synthetic.

Antibodies which are specific for a target of interest may be obtained using techniques which are standard in the art. Methods of producing antibodies include immunising a mammal (e.g. mouse, rat, rabbit) with the protein or a fragment thereof or a cell or virus which expresses the protein or fragment. Antibodies may be obtained from immunised animals using any of a variety of techniques known in the art, and screened, for example using binding of antibody to antigen of interest.

An "antigen binding domain" is the part of an antibody which comprises the area which specifically binds to and is complementary to part or all of an antigen. Where an antigen is large, an antibody may only bind to a particular part of the antigen, which part is termed an epitope. An antigen binding domain may be provided by one or more antibody variable domains. An antigen binding domain may comprise an antibody light chain variable region (VL) and an antibody heavy chain variable region "Specific" is generally used to refer to the situation in which one member of a specific binding pair will not show any significant binding to molecules other than its specific binding partner(s), e.g., has less than about 30%, preferably 20%, 10%, or 1% cross-reactivity with any other molecule.

The specific binding members of the invention will preferably be, in accordance with the present invention, in "isolated" form. Members will generally be free or substantially free of material with which they are naturally associated such as other polypeptides with which they are found in their natural environment, or the environment in which they are prepared (e.g. cell culture) when such preparation is by recombinant DNA technology practised in vitro or in vivo.

Thus the specific binding member of the invention is preferably an antibody, or fragment thereof. Thus, for example in (ii) the specific binding partner member may be an antibody, or fragment thereof, having an antigen binding domain specific for prostate tissue. For example in (iii) the specific binding member may be an antibody, or fragment thereof, having an antigen binding domain specific for MCM.

The antibody may be a polyclonal antibody, monoclonal antibody, single chain antibody or fragment of any of the foregoing. Preferably the specific binding member is a monoclonal antibody having an antigen binding domain specific for MCM. Monoclonal antibodies specific for MCM are known in the art, for example, anti-MCM2 antibody used in the present study derived from the clone D112A3 originating in the MRC Cancer Cell Unit, Hutchison/MRC Research Centre, Hills Road, Cambridge CB2 0XZ.

The production of monoclonal antibodies using hybridoma cells is well-known in the art. The methods used to produce monoclonal antibodies are disclosed by Kohler and Milstein in Nature 256, 495-497 (1975) and also by Donillard and Hoffman, "Basic Facts about Hybridomas" in Compendium of Immunology V.II ed. by Schwartz, 1981, which are incorporated by reference.

In a method of the invention, the specific binding members of the invention may be labelled with a detectable label, for example a radiolabel such as $I^{125}$ or $I^{131}$ or 99Tc, which may be attached to specific binding members of the invention using conventional chemistry known in the art of antibody imaging. Labels also include enzyme labels such as horseradish peroxidase or alkaline phosphatase. Labels further include chemical moieties such as biotin which may be detected via binding to a specific cognate detectable moiety, e.g. labelled avidin.

The reactivities of a specific binding member such as an antibody on normal and test samples may be determined by any appropriate means. Other labels include fluorochromes, phosphor or laser dye with spectrally isolated absorption or emission characteristics. Suitable fluorochromes include fluorescein, rhodamine, phycoerythrin and Texas Red. Suitable chromogenic dyes include diaminobenzidine. Other labels include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. In the examples described below, alkaline phophatase or horseradish peroxidase have been employed.

The cell count may be determined by any appropriate means including, but not limited to, immunocytochemical means, flow cytometry and image cytometry. Preferably the cell count is determined by flow cytometry or an automated cell counter.

The methods of the invention may be used in combination with a Pap (Papanicolaou) stain to provide histological staining of the cells using a multichromatin stain. Methods for Pap staining of cells are known in the art including Coleman and Chapman 1989 (Coleman Dulcie; Chapman, Patricia (1989), Clinical Cytotechnology, Butterworth & Co. pp 80-82) and Carson and Hladik 2009 (Carson Freida L; Hladik, Christa (2009), Histotechnology: A Self-Instructional Text (3 ed.), Hong Kong: American Society for Clinical Pathology Press. pp. 361-3363).

Thus the invention provides a method of detecting a subject suffering from, or at risk of suffering from, bladder cancer the method comprising
 i) providing a body fluid sample isolated from a subject;
 ii) isolating cells from said sample to provide a cell sample;
 iii) contacting the sample with a specific binding member capable of binding to a minichromosome maintenance (MCM) polypeptide(s) and optionally contacting the cells with a Pap stain;
 iv) determining the binding of said specific binding member to the cell sample;
 v) counting those cells in said cell sample which bound to said specific binding member to provide a cell count;
 vi) determining, based on the cell count, whether the subject has, or is at risk of having, bladder cancer.

The invention further provides a method to diagnose and treat a subject suffering, or suspected from suffering, from bladder cancer comprising the steps:
 i) providing a fluid sample isolated from a subject;
 ii) isolating cells from said sample to provide a cell sample;
 iii) contacting the sample with a specific binding member capable of binding to a mini chromosome maintenance (MCM) polypeptide(s);
 iv) determining the binding of said specific binding member to the cell sample;
 v) counting those cells in said cell sample which bound to said specific binding member to provide a cell count;
 vi) determining, based on the cell count, whether the subject has, or is at risk of having, bladder cancer;
 vii) determining a treatment regime to prevent and/or treat the subject's suspected bladder cancer/cancer respectively; and
 viii) administering said treatment regime to prevent and/ or treat the subject's suspected bladder cancer/cancer respectively.

A further aspect of the invention provides a method for detecting or determining the presence of bladder cancer cells in a sample of body fluid from a subject comprising:
(i) isolating cells from said sample to provide a cell sample;
(ii) contacting said cell sample with a specific binding member capable of binding a minichromosome maintenance 2 (MCM 2) polypeptide(s) and/or a minichromosome maintenance 7 (MCM 7) polypeptide(s); and
(iii) determining the binding of said specific binding member(s) to the cell sample.

Where the specific binding member capable of binding minichromosome maintenance 7 (MCM7) polypeptide and/ or a minichromosome maintenance 2 (MCM 2) polypeptide, for example an anti-MCM7 and/or anti-MCM2 antibody, is determined to have bound to the sample, this is indicative of bladder cancer in the subject. Thus the invention provides a method for determining an early prognosis of progression of bladder cancer in a subject the method comprising detecting or determining the presence of bladder cancer cells in a sample of body fluid, for example urine, from said subject according to the method of the first aspect of the invention. The subject may be a cohort of patients selected from patients presenting with either (i) no symptoms of bladder cancer, (ii) haematuria or lower urinary tract symptoms (e.g. infection), or (iii) patients undergoing follow up cystoscopic analysis for urothelial neoplasia.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention will now be described by way of example only with reference to the following figures.

FIGS. 1-6 are dot plots illustrating the data obtained from patients attending the Gross Haematuria Clinic with individual MCM threshold counts of 10, 30, 50, 100, 200 and 400 respectively.

FIGS. 7-12 are dot plots illustrating the data obtained from patients attending the Cystoscopic Surveillance Clinic all of whom had urine testing based on fresh voided urine specimens and MCM thresholds covering the same range of stained MCM cells, 10, 30, 50, 100, 200 and 400 respectively.

FIGS. 13-18 are dot plots illustrating the data obtained from normal subjects aged 50+ years taken as a population based control for patients who present either with gross haematuria or for cystoscopic surveillance having had biopsy positive disease in the past.

FIGS. 19-24 are dot plots illustrating the data obtained from patients with no evidence of renal tract disease (and in particular no history of bladder cancer present or past and no evidence of recent urinary tract infection) covering the same range of stained MCM cells 10, 30, 50, 100, 200 and 400 respectively.

FIGS. 25-30 are dot plots illustrating the data obtained from patients presenting to the GH clinic and who are found to have Microscopic Haematuria (MH), representing up to 70% of the GH Clinic patients. These patients have a very low incidence of TCC, and with a normal cytoscopy do not usually have a biopsy taken at clinic. This illustrates the value of MCM as an additional diagnostic aid in the management of patients under investigation for TCC and may obviate the need for routine cystoscopy.

EXAMPLES

Example 1

Materials and Methods

In the present study, conducted at Addenbrookes Hospital, Cambridge, a total of 246 patients who routinely attended the surgical outpatient department (Department of Urology, Addenbrookes Hospital, Cambridge) were investigated for the possible presence or recurrence of bladder cancer. Earlier work had indicated that the biology of these patients, all of whom had Transitional Cell Carcinoma (TCC) could be conveniently divided into two main groups—
1. Those who presented for the first time to the clinic with Gross Haematuria (GH patients), i.e. frank evidence of blood in the urine, for urgent review of the possibility of bladder cancer, and
2. Those patients who returned to the clinic having had a biopsy positive diagnosis of bladder cancer at some point in the past, and had had treatment depending on the nature and aggressiveness of the tumour and were now returning for cystoscopic review (CS patients).

These patients were followed up having undergone a routine full investigation consistent with best practice in the clinic. Such investigation involved a full systematic enquiry, full physical examination, intravenous urogram, electrocardiogram (ECG) and chest X-ray where indicated, as well as the possibility of a routine bladder scan and/or flexible cystoscopy as an outpatient on initial presentation or on cystoscopic follow-up, together with a whole volume urine collection for routine urinary cytology and in this instance, MCM antibody investigation.

Urine samples were collected in the ward on admission to the Unit (0830-1230 hours) or following admission to the surgical outpatient department, the whole sample of urine was thereafter transferred to the laboratory within 1-2 hours of void, and a 50 mls sample in the laboratory produced adequate numbers of bladder epithelial cells in all samples collected.

Routine laboratory practice was then undertaken in which centrifugation of urine (2500 rpm×10 minutes) took place by designated skilled individuals in the laboratory. 50 mls from whole volume voided urine was delivered to the laboratory and divided between Falcon tubes for different experiments. Following centrifugation the supernatant was decanted into Virkon and the pooled cellular material was washed into one Falcon tube using Cytolyt. The tube was then topped up with Cytolyt, vortexed for five minutes, re-centrifuged and the supernatant again decanted into Virkon. The cell pellet was then re-suspended and following preparation of two PreservCyt vials (one for PAP stain and one for ICC stain) the cell deposit was then dispensed into the prepared vials, one drop at a time, alternate vials, until all the cell deposit was used up. Two ThinPrep slides were then prepared, one for PAP stain and one for ICC stain, and processed on the ThinPrep 2000 machine. The slide for PAP staining was placed in acetic alcohol while the slide for ICC was fixed with spirit in the TP 2000 bath, drained then fixed by using a Surgipath coated spray and left flat to dry naturally. The processing preparation and staining of urothelial cells in a liquid based cytology medium (LBC) was carried out on a Dako autostainer. Preparation had four sections.

a. Prestained protocol histology slides. Slides were re-hydrated from xylene using a spirit and water sequence with antigen retrieval for 10+10 minutes in a pH6 citrate buffer in a microwave. Slides were then washed with water and loaded onto the autostainer.

b. Prestained protocol cytology slides. Slides were first immersed in 50% ethanol for 5 minutes, rinsed in distilled water and placed in TBS. Antigen retrieval in EDTA buffer at pH7.8 was carried out and slides were then allowed to cool at room temperature for 20 minutes. Slides were rinsed in water followed by buffer before being placed on the autostainer.

c. Autostainer Staining Protocol (Envision HRP) Dako Kit 5007. The sequence for staining involved a peroxidase block with $H_2O_2$ for 5 minutes with additional $H_2O_2$ for a further 5 minutes. Slides were then rinsed ×3 with TBS buffer, antibodies and controls added for 60 minutes, rinsed ×2 with TBS buffer and Envision HRP added for 30 minutes. Finally, slides were rinsed ×2 with TBS buffer and DAB substrate added for 5 minutes.

d. Post-Stain Protocol. Following the initial autostainer staining protocol, slides were rinsed in water, immersed in $CuSO_4$ for 3 minutes, rinsed in water and counterstained with haematoxylin for 10 seconds. Slides were then rinsed in water followed by Scott's tap water for 40 seconds, rinsed in water, dehydrated through spirit ×2, alcohol and xylene. Finally slides were coverslipped by DPX.

The detailed methodology is as follows:

1. The current protocol used in the detection of bladder cancer cells in urine is based on staining clinical epithelial BC cells with an MCM2/DAB (Diaminobenzidine) combination.
2. The binding of the MCM2 antibody (The MRC Cancer Cell Unit, Hutchison MRC Research Centre, Hills Road, Cambridge, CB2 OXZ) in the nucleus and the effect of the chromophore DAB can be visualized by a dark brown nuclear stain under white light microscopy.
3. The methodology for applying the ICC stain to epithelial bladder cells is as follows:

A. The pre-staining protocol involves slides immersed in 50% methanol for 5 minutes, rinsed in distilled water, and placed in EDTA buffer at pH 7.8 for antigen retrieval for 45 minutes at 95 degree C.

B. After 45 minutes, the container is allowed to cool at room temperature for 20 minutes, rinsed in distilled water before placing the slides on the autostainer.

C. The staining procedure involves a DAKO Envision Kit 5007, with peroxidase block using H2O2 added to the slides for 5 minutes and rinsed with TBS buffer ×3.

D. Following the blocking procedure, the slides are treated with MCM2 antibody at a dilution of 1/400, incubated for 60 minutes and then rinsed again with TBS buffer ×3.

E. Following this procedure, Envision HRP is added to the slides for 30 minutes.

F. The slides are then rinsed with buffer ×2 before the addition of DAB for 10 minutes.

G. The slides are again rinsed with buffer ×1 and distilled water ×1, Copper sulphate solution is added to the slides for 5 minutes and then rinsed with distilled water.

H. After staining is completed, the slides are counterstained with PAP according to a standard non-gynae SOP.

The detailed statistics of this study have been evaluated using a liquid based cytology slide preparation and MCM2 antibody, as described. The principal analysis was carried out using SPSS as the statistical package of choice. Data relating to the age distributions, the gender distributions and the biopsy outcomes in each of the patient groups (16 positive biopsies in the GH Clinic and 24 positive biopsies in the CS Clinic) were annotated.

The data was collected in five sections namely, patients who attended the Gross Haematuria Clinic and who had been found to have no tumour; those who attended the Gross Haematuria Clinic and had been found to have TCC of the bladder; those who attended the Gross Haematuria Clinic with a provisional diagnosis of Microscopic Haematuria and had been found to have no tumour; those who attended the Cystoscopic Surveillance Clinic and had been found to have no tumour; and a fifth group in which attendance at the Cystoscopic Surveillance Clinic had shown the presence of tumour.

Results

Gross Haematuria (GH) Patients

In patients who presented for the first time with gross haematuria (fresh and visible blood in the urine of patients presenting to the clinic) 6 MCM thresholds over a range of 10 to 400 MCM stained cells were exemplified. In each case the percentage sensitivity, i.e. those patients with known tissue positive bladder cancer, and the percentage specificity, i.e. those patients with no evidence of tissue based bladder malignancy, were measured against biopsy data in each case.

MCM Threshold=10

This exemplifies that where an MCM stained cell threshold of 10 MCM positive cells is used, then 100% sensitivity is achieved against positive biopsy with a 51% specificity in that group of patients.

MCM Threshold=30

In those patients in which 30 or more stained MCM cells are present in routine liquid based cytology slides against positive biopsy, 100% of all such patients will be detected using this test. At the same time, in such patients where biopsy negative information is available, there is a 72% specificity outcome detected by MCM testing.

MCM Threshold=50

In patients with an MCM threshold of 50 stained cells or above in biopsy positive patients with bladder cancer, there is a 92% sensitivity of detecting such malignancy. At the same time, in those patients who are biopsy negative with an MCM threshold of less than 50 stained cells there is an 83% chance of defining such negative findings.

MCM Threshold=100

With an MCM threshold of 100 or more stained cells against biopsy positive tissue, there is a 75% sensitivity in detecting such positive outcomes. Correspondingly, in the same group of patients with a negative biopsy outcome there is an 89% specificity indicating that no tumour is present.

MCM Threshold=200

In patients where an MCM threshold of 200 or more stained cells is present, there is a 67% sensitivity against biopsy positive tissue of detecting malignancy in these patients. Correspondingly, there is a 98% specificity indicating that in those patients with less than 200 stained MCM cells present, then such malignancy does not exist.

MCM Threshold=400

In this instance where the MCM threshold is 400 or more there is a 42% sensitivity against positive biopsy in detecting malignancy in such patients. At the same time, there is a 98% specificity recorded in those patients who have less than 400 MCM stained cells against negative biopsy noted.

Cystoscopic Surveillance (CS) Patients

In this group of patients there is a history of known biopsy positive bladder cancer and this usually is of the commonest type, namely Transitional Cell Carcinoma (TCC). Other types of cancer, though present, may also be detected where malignant cells are shed into urine.

MCM Threshold=10

Where an MCM stained threshold of 10 stained cells is present, there is a 100% sensitivity of detecting those patients who are biopsy positive in this group. Equally, there is a 41% specificity of detecting those patients who do not have a recurrence of bladder cancer in a biopsy negative group.

MCM Threshold=30

With an MCM threshold of 30 or more stained cells, there is a 95% sensitivity against biopsy positive tissue of detecting such malignancy in these patients. At the same time, there is a 54% specificity of indicating that in biopsy negative patients there is no such recurrence of bladder tumour.

MCM Threshold=50

In these patients, where the MCM threshold is 50 or more stained cells, there is a 90% sensitivity correlation between biopsy positive tissue and MCM stained cells. At the same time there is a 69% specificity against biopsy negative tissue in such patients indicating that no such recurrence of bladder tumour is evident.

MCM Threshold=100

In this group of patients where the MCM threshold is 100 or more stained cells, there is 90% sensitivity against biopsy positive material of detecting malignancy in these patients. At the same time there is an 81% specificity in biopsy negative individuals indicating that a recurrence of bladder tumour is not present.

MCM Threshold=200

In these patients with an MCM threshold of 200 or more stained cells, there is a 90% sensitivity of detecting those patients with biopsy positive malignancy in tissue samples. At the same time, there is a 96% specificity in indicating in biopsy negative individuals that a recurrence has not taken place.

MCM Threshold=400

In this group of patients there is a 53% sensitivity indicating that in biopsy positive patients recurrence of bladder tumour has occurred. At the same time, there is a 98% specificity in biopsy negative patients of detecting those patients in whom recurrence has not occurred.

Normal Subjects

A third group of subjects was asked to pass a standard 50 mls sample of urine (exactly as patients had done in the Urology outpatient department both at Aberdeen Royal Infirmary and Addenbrookes Hospital, Cambridge) the only requirement for which was that such individuals had no recent or past history of urological disease, and in particular infection. This group acted as normal controls for all patients in the bladder cancer test series both those presenting with gross haematuria (first time attendance) and those who return to the clinic for cystoscopic review. The urines of all such subjects were analysed in exactly the same way and by the same methodology using the same stain (MCM2) and within the same timeframe (less than 4 hours).

MCM Threshold=10

Biopsy validation of the absence of bladder tumour could not be undertaken in this group of normal subjects, and no cystoscopic examination was undertaken. The data therefore represents MCM cell counts indicating both sensitivity and specificity at a range of different MCM thresholds. With the MCM threshold of 10, 58% of normal adults had a stained MCM cell count indicating the possibility of infection or malignancy in routine urine samples. At the same time there was a 42% specificity reading indicating that no such abnormality existed.

MCM Threshold=30

At a threshold of 30 stained MCM cells in normal urines there was a 33% sensitivity and a 67% specificity of such normal values. This confirms part of the spread of comparative data whereby as the specificity indicating no abnormal findings increases so the sensitivity indicating the possibility of malignancy decreases.

MCM Threshold=50

In these urine samples with an MCM stained cell count of 50 or more, 23% of samples showed some staining and appropriate sensitivity while 77% indicated the specificity as having no likely malignant outcome.

MCM Threshold=100

Where 100 or more stained MCM cells were noted in normal urines, there was a 15% sensitivity indicating a possible outcome for further investigation while at the same time an 85% specificity indicating that there were no issues for concern.

MCM Threshold=200

Where 200 or more MCM stained cells were noted then there was a 4% sensitivity of possible inflammation or malignancy and a 96% specificity indicating that no such concern or damage was evident.

MCM Threshold=400

Where 400 or more stained MCM cells were noted in the urine of normal subjects, 0% sensitivity indicated no evidence of concern and in particular malignancy, and a 100% specificity indicating that no such damage or concerns existed.

By way of explanation, the percentage sensitivity, i.e. the ability to determine the presence of bladder cancer, was assessed against the presence of a positive histological outcome on biopsy material. Likewise, in these patients specificity, i.e. the absence of evidence of bladder cancer was assessed against the evidence of biopsy negative tissue histology. The exception to this circumstance obtained in those subjects who were deemed normal, i.e. no evidence of urological disease, had the same urine assessments by the same counting methods but in the absence of either cystoscopy or biopsy proof of disease.

The data for the Gross Haematuria and the Cystoscopic Surveillance patient groups demonstrated that as sensitivity increases then the specificity decreases. Conversely, in those patients who have had biopsy proven bladder cancer in the past, as the specificity increases then the sensitivity decreases.

The data are summarised by individual patient and by group analysis in the dotplot of MCM count vs clinic and outcome (biopsy analysis)—data not shown. A threshold line is drawn at a MCM cell count of 50 stained cells or more per slide. Each of the categories have been analysed in relation to biopsy outcomes whether in the GH Clinic or the CS Clinic or normal subjects, and all are related to an MCM stained cell count on the appropriate cytology slide of 50 stained MCM cells.

74% of negative biopsies in the GH clinic are correctly identified by MCM<50 and 26% result in false positives.

94% of positive biopsies in the GH clinic are correctly identified by MCM≥50 and 6% result in false negatives.

67% of negative biopsies in the CS clinic are correctly identified by MCM<50 and 33% result in false positives.

83% of positive biopsies in the CS clinic are correctly identified by MCM≥50 and 17% result in false negatives.

77% of normal urines showed no evidence of MCM stained characteristics indicative of abnormality while 23% of normal urines indicated that there were ≥50 MCM stained cells present.

A range of MCM cell counts from 10 stained MCM cells to 400 MCM stained cells was evaluated and it was found that where more than 50 MCM stained cells were present on any one slide, then the frequency of malignancy increased. It was surprisingly found that at an MCM threshold of 50, perfect agreement between MCM vs PAP (routine cytology), was obtained for positive outcomes in those patients who present for the first time with Gross Haematuria to the surgical outpatient department. Moreover it was found that at an MCM threshold of 200, perfect agreement between MCM vs PAP (routine cytology), was obtained for positive outcomes in those patients who had a history of known biopsy positive bladder cancer.

In addition, it was determined at the outset of the study that only cases with a total cell count of 1000 or more cells (called 'cell adequacy of 1000') were analysed to determine MCM positivity or otherwise. This ensured better cytology quality and was approved and regulated by an independent Cytopathologist.

The analyses herein was repeated and the results are shown in Example 2.

Example 2

Materials and Methods

In the present study, conducted at four different sites across the UK, namely Bradford Royal Infirmary, Addenbrookes Hospital, Cambridge, Homerton Hospital, London, and the Western General Hospital, Edinburgh, a total of 107 patients who routinely attended the surgical outpatient Department of Urology at each hospital, were investigated for the possible presence or recurrence of bladder cancer. Earlier work had indicated that the biology of these patients, all of whom were investigated for Transitional Cell Carcinoma (TCC) or were returning for cystoscopic surveillance of biopsy positive TCC, could be conveniently divided into two main groups—
1. Those who presented for the first time to the clinic with Gross Haematuria (GH patients), i.e. frank evidence of blood in the urine, for urgent review of the possibility of bladder cancer, and included in this group those patients who presented for the first time with Microscopic Haematuria, i.e. biochemical evidence of blood in the urine without visual diagnosis, and
2. Those patients who returned to the clinic having had a biopsy positive diagnosis of bladder cancer at some point in the past, and had had treatment depending on the nature and aggressiveness of the tumour and were now returning for cystoscopic review (CS patients).

These patients were followed up having undergone a routine full investigation consistent with best practice in the clinic. Such investigation involved a full systematic enquiry, full physical examination, intravenous urogram, electrocardiogram (ECG) and chest X-ray where indicated, as well as the possibility of a routine bladder scan and/or flexible cystoscopy as an outpatient on initial presentation or on cystoscopic follow-up, together with a whole volume urine collection for routine urinary cytology and in this instance, MCM antibody investigation.

Urine samples were collected either in the ward on admission to the Unit (0830-1230 hours) or following admission to the surgical outpatient department of the relevant hospital. The whole sample of urine was thereafter transferred to the laboratory within 1 hour of void, and a 50 mls sample in the laboratory produced adequate numbers of bladder epithelial cells in all samples collected.

Routine laboratory practice was then undertaken in which centrifugation of urine (2500 rpm×10 minutes) took place by designated skilled individuals in the laboratory. The supernatant fluid was then poured out and the cell pellet added to SurePath fixative. The sample was left for 15 minutes and then re-centrifuged for ten minutes at 2500 rpm. Once more the supernatant fluid was poured off and the remaining cell pellet vortexed in a sealed sample tube. The sample tube was then added into the bucket of the Tripath machine, the slide and the settling chamber were entered and the labelled tube for EA/OG was removed from DI water and placed in a corresponding reagent bottle. The thin tube labelled "Hema" was also removed out of DI water and placed in a bottle for haematoxylin. The operator then ensured that the pipette tip box on the SurePath machine remained flat, the waste bucket pump was turned on, the computer was accessed and the programme specific for SurePath urine cytology analysis was then carried out. The remaining protocol for the Tripath (SurePath) system was then carried out using the standard non gynaecological programme SOP. Following completion of the Tripath non gynaecological programme SOP a standard clean up system for the Tripath approach to slide preparation was carried out.

The detailed statistics of this study have been evaluated using a liquid based cytology slide preparation and MCM2 antibody, as described. The principal analysis was carried out using SPSS as the statistical package of choice. Data relating to the age distributions, the gender distributions and the biopsy outcomes in each of the patient groups were annotated.

The data was collected in six sections namely, patients who attended the Gross Haematuria Clinic and who had been found to have no tumour; those who attended the Gross Haematuria Clinic and had been found to have TCC of the bladder; those who attended the Gross Haematuria Clinic with a provisional diagnosis of Microscopic Haematuria and had been found to have no tumour; those who attended the Cystoscopic Surveillance Clinic and had been found to have no tumour; those who attended the Cystoscopic Surveillance Clinic and had been found to have TCC of the bladder; and a sixth group in which a group of normal volunteers aged over 50 years were also selected from the same clinics and in the absence of any symptoms related to urinary tract infection or urinary tract disease, were used as the normal control subjects throughout the course of this evaluation.

Results

Gross Haematuria (GH) Patients

In patients who presented for the first time with gross haematuria (fresh and visible blood in the urine of patients presenting to the clinic) 6 MCM thresholds over a range of 10 to 400 MCM stained cells were exemplified. In each case the percentage sensitivity, i.e. those patients with known tissue positive bladder cancer, and the percentage specificity, i.e. those patients with no evidence of tissue based bladder malignancy, were measured against biopsy data in each case.

MCM Threshold=10 (FIG. 1)

This exemplifies that where an MCM stained cell threshold of 10 MCM positive cells is used, then 100% sensitivity is achieved against positive biopsy with a 31% specificity in that group of patients.

MCM Threshold=30 (FIG. 2)

In those patients in which 30 or more stained MCM cells are present in routine liquid based cytology slides against positive biopsy, 100% of all such patients will be detected using this test. At the same time, in such patients where biopsy negative information is available, there is a 63% specificity outcome detected by MCM testing.

MCM Threshold=50 (FIG. 3)

In patients with an MCM threshold of 50 stained cells or above in biopsy positive patients with bladder cancer, there is an 83% sensitivity of detecting such malignancy. At the same time, in those patients who are biopsy negative with an MCM threshold of less than 50 stained cells there is an 81% chance of defining such negative findings, i.e. specificity.

MCM Threshold=100 (FIG. 4)

With an MCM threshold of 100 or more stained cells against biopsy positive tissue, there is a 83% sensitivity in detecting such positive outcomes. Correspondingly, in the same group of patients with a negative biopsy outcome there is an 81% specificity indicating that no tumour is present.

MCM Threshold=200 (FIG. 5)

In patients where an MCM threshold of 200 or more stained cells is present, there is a 83% sensitivity against biopsy positive tissue of detecting malignancy in these patients. Correspondingly, there is a 88% specificity indicating that in those patients with less than 200 stained MCM cells present, then such malignancy does not exist.

MCM Threshold=400 (FIG. 6)

In this instance where the MCM threshold is 400 or more there is 83% sensitivity against positive biopsy in detecting malignancy in such patients. At the same time, there is a 87% specificity recorded in those patients who have less than 400 MCM stained cells against negative biopsy noted.

Cystoscopic Surveillance (CS) Patients

In this group of patients there is a history of known biopsy positive bladder cancer and this usually is of the commonest type, namely Transitional Cell Carcinoma (TCC). Other types of cancer, though present, may also be detected where malignant cells are shed into urine.

MCM Threshold=10 (FIG. 7)

Where an MCM stained threshold of 10 stained cells is present, there is a 100% sensitivity of detecting those patients who are biopsy positive in this group. Equally, there is a 39% specificity of detecting those patients who do not have a recurrence of bladder cancer in a biopsy negative group.

MCM Threshold=30 (FIG. 8)

With an MCM threshold of 30 or more stained cells, there is 100% sensitivity against biopsy positive tissue of detecting such malignancy in these patients. At the same time, there is a 64% specificity of indicating that in biopsy negative patients there is no such recurrence of bladder tumour.

MCM Threshold=50 (FIG. 9)

In these patients, where the MCM threshold is 50 or more stained cells, there is a 100% sensitivity correlation between biopsy positive tissue and MCM stained cells. At the same time there is a 82% specificity against biopsy negative tissue in such patients indicating that no such recurrence of bladder tumour is evident.

MCM Threshold=100 (FIG. 10)

In this group of patients where the MCM threshold is 100 or more stained cells, there is a 91% sensitivity against biopsy positive material of detecting malignancy in these patients. At the same time there is an 91% specificity in biopsy negative individuals indicating that a recurrence of bladder tumour is not present.

MCM Threshold=200 (FIG. 11)

In these patients with an MCM threshold of 200 or more stained cells, there is a 91% sensitivity of detecting those patients with biopsy positive malignancy in tissue samples. At the same time, there is a 93% specificity in indicating in biopsy negative individuals that a recurrence has not taken place.

MCM Threshold=400 (FIG. 12)

In this group of patients there is a 82% sensitivity indicating that in biopsy positive patients recurrence of bladder tumour has occurred. At the same time, there is a 93% specificity in biopsy negative patients of detecting those patients in whom recurrence has not occurred.

Combined Clinics (GH+CS)

In this group of patients, the data from those patients who initially presented with gross haematuria (GH) for the first time, i.e. fresh and visible blood in the urine of patients presenting to the clinic, and in addition, those patients who return to the clinic for cystoscopic surveillance (CS) having had a positive biopsy for tumour earlier and some subsequent treatment, these cases are presented as a single group of patients with transitional cell biopsy positive carcinoma.

MCM Threshold=10 (FIG. 13)

Where an MCM stained threshold of 10 stained cells is present, there is a 100% sensitivity of detecting those patients who are biopsy positive in this group. Equally, there is a 37% specificity of detecting those patients who do not have a recurrence of bladder cancer in a biopsy negative group.

MCM Threshold=30 (FIG. 14)

With an MCM threshold of 30 or more stained cells there is 100% sensitivity against biopsy positive tissue of detecting such malignancy in these patients. At the same time there is a 63% specificity of indicating that in biopsy negative patients there is no such recurrence of bladder tumour.

MCM Threshold=50 (FIG. 15)

In these patients where the MCM threshold is 50 or more stained cells, there is a 94% sensitivity correlation between biopsy positive tissue and MCM stained cells. At the same time there is 82% specificity against biopsy negative tissue in such patients indicating that no such recurrence of bladder tumour is evident.

MCM Threshold=100 (FIG. 16)

In this group of patients where the MCM threshold is 100 or more stained cells, there is an 88% sensitivity against biopsy positive material detecting malignancy in these patients. At the same time, there is an 88% specificity in biopsy negative individuals indicating that a recurrence of bladder tumour is not present.

MCM Threshold=200 (FIG. 17)

In these patients with an MCM threshold of 200 or more stained cells, there is an 88% sensitivity of detecting those patients with biopsy positive malignancy in tissue samples. At the same time, there is a 92% specificity in indicating in biopsy negative individuals that a recurrence of tumour has not taken place.

MCM Threshold=400 (FIG. 18)

In this group of patients, there is an 82% sensitivity indicating that in biopsy positive patients, recurrence of bladder tumour has occurred. At the same time, there is a 92% specificity in biopsy negative patients of detecting those patients in whom recurrence has not occurred.

Normal Subjects (No Evidence Bladder Tumour)

A group of normal subjects aged 50+ years was taken as a population based control for patients who present either with gross haematuria or for cystoscopic surveillance having had biopsy positive disease in the past. The data on such subjects (so-called normal clinic) was annotated in exactly the same way other than sensitivities, i.e. evidence of positive tumour on biopsy was not recorded. This relates to the fact that these subjects had neither cystoscopy nor biopsy undertaken as part of the normal control mechanism.

MCM Threshold=10 (FIG. 19)

In this group of subjects where an MCM stained cell threshold of 10 MCM positive cells is used, there is an 18% specificity confirming that no disease exists. The remaining subjects in this group may have had associated urological infection or contamination of one clinical sort or another, even though on direct questioning such symptoms were denied.

MCM Threshold=30 (FIG. 20)

In these subjects in which 30 or more stained MCM cells are present, in routine liquid based cytology slides, 36% of subjects showed a specificity indicating no evidence of bladder tumour.

MCM Threshold=50 (FIG. 21)

In subjects with an MCM threshold of 50 stained cells or above, there was a 55% specificity indicating no evidence of tumour occurrence.

MCM Threshold=100 (FIG. 22)

In this group of subjects with an MCM threshold of 100 or more stained cells in urine, there is a 91% specificity indicating no evidence of bladder cancer.

MCM Threshold=200 (FIG. 23)

In this group of subjects where an MCM threshold of 200 or more stained cells is present, there is a specificity of 91% indicating no evidence of malignant bladder disease.

MCM Threshold=400 (FIG. 24)

In this instance, where the MCM threshold is 400 or more, there is specificity of 91% indicating that no evidence of bladder cancer exists in these subjects.

Microscopic Haematuria (MH) Patients

In this group of patients, there is a particularly low frequency of TCC, even though these patients may constitute anything up to 70% of referrals to the GH clinic. They therefore comprise an important group of patients in whom cystoscopy is commonly negative, i.e. no tumour seen, and hence biopsy is seldom undertaken. The use of MCM as an additional diagnostic test is of further benefit in confirming the absence of bladder cancer.

MCM Threshold=10 (FIG. 25)

In this group of patients where an MCM threshold of 10 or more stained cells is present, there is an 80% specificity indicating that no evidence of bladder cancer exists. Sensitivity cannot be given in the absence of biopsy evidence.

MCM Threshold=30 (FIG. 26)

In this group of patients where an MCM threshold of 30 or more stained cells is present, there is a 90% specificity indicating that no evidence of bladder cancer exists.

MCM Threshold=50 (FIG. 27)

In this group of patients where an MCM threshold of 50 or more stained cells is present, there is a 90% specificity indicating that no evidence of bladder cancer exists.

MCM Threshold=100 (FIG. 28)

In this group of patients where an MCM threshold of 100 or more stained cells is present, there is a 90% specificity indicating that no evidence of bladder cancer exists.

MCM Threshold=200 (FIG. 29)

In this group of patients where an MCM threshold of 200 or more stained cells is present, there is a 93% specificity indicating that no evidence of bladder cancer exists.

MCM Threshold=400 (FIG. 30)

In this group of patients where an MCM threshold of 400 or more stained cells is present, there is a 97% specificity indicating that no evidence of bladder cancer exists.

By way of explanation of FIGS. 1 to 12, the percentage sensitivity, i.e. the ability to determine the presence of bladder cancer, was assessed against the presence of a positive histological outcome on biopsy material. Likewise, in these patients specificity, i.e. the absence of evidence of bladder cancer was assessed against the evidence of biopsy negative tissue histology. In FIGS. 13-18, the overall percentage sensitivity and specificity is annotated in all patients with evidence of biopsy positive TCC or who are returning for cystoscopic surveillance. In addition, in FIGS. 19-24, a group of normal subjects aged 50+ years are used as a comparator group and in particular have no previous or present history of urological disease. In FIGS. 25-30, a group of patients who attended the GH clinic and were noted to have Microscopic Haematuria demonstrate the known low incidence of TCC and, in the absence of biopsy material on the basis of a negative cystoscopy, show corresponding high specificity with increasing MCM cell counts.

The data for the Gross Haematuria and the Cystoscopic Surveillance patient groups demonstrated that as sensitivity increases then specificity decreases. Conversely, in those patients who have had biopsy proven bladder cancer in the past, as the specificity increases then sensitivity decreases.

The data are summarised by individual patient and by group analysis in the dotplot of MCM count vs clinic and outcome (biopsy analysis).

81% of negative biopsies in the GH clinic are correctly identified by MCM<50 and 19% result in false positives.

83% of positive biopsies in the GH clinic are correctly identified by MCM≥50 and 17% result in false negatives.

82% of negative biopsies in the CS clinic are correctly identified by MCM≤50 and 18% result in false positives.

100% of positive biopsies in the CS clinic are correctly identified by MCM≥50 and 0% result in false negatives.

55% of normal urines showed no evidence of MCM stained characteristics indicative of abnormality while 45% of normal urines indicated that there were ≥50 MCM stained cells present.

90% of urines in the MH clinic showed no evidence of MCM stained characteristics indicative of abnormality while 10% indicated that there were ≤50 MCM stained cells present.

A range of MCM cell counts from 10 stained MCM cells to 400 MCM stained cells was evaluated and it was found that where more than 50 MCM stained cells were present on any one slide, then the frequency of malignancy increased irrespective of disease origin, i.e. first clinic presentation or cytoscopic surveillance. When MCM was compared with PAP evaluation at a threshold of 50 or more stained cells in the GH clinic 77.8% of TCC were identified, and 91.7% showed a specificity with no evidence of tumour.

In addition, it was found that at an MCM threshold of 200 or more stained cells in the CS clinic, 84.6% of TCC were identified between MCM vs PAP (routine cytology), and importantly in this group of patients 97.2% were identified as having no recurrence of bladder tumour.

In the combined clinics (GH and CS) the combination of MCM and PAP showed a correlation of 81.8% in determining malignant change, with a specificity of 95.8% in defining no evidence of malignancy.

It is important to note that it was determined at the outset of the study that only cases with a total cell count of 5000 or more cells (called 'cell adequacy of 5000') were analysed to determine MCM positivity or otherwise. This ensured better cytology quality and was approved and regulated by an independent Cytopathologist.

Prognostic Indicators of MCM in Bladder Cancer

As part of the routine follow-up of patients reviewed in the Urology Clinic, follow-up is conducted on those patients who in the past have had biopsy positive bladder cancer. The pattern of follow-up for such patients has indicated that best practice involves a series of visits to the clinic for repeat examination and cystoscopy on average four times per year for the first two years, twice per year for years three and four, and annually thereafter where no evidence of recurrent tumour is found. However, it was of interest that in a number of cases in either centre, some patients presented with no evidence of histologically proven bladder cancer or indeed a recurrence of such cancer but who were notably MCM positive on urine test. In one centre, five such patients have come under review in the last eighteen months, all derived from the CS Clinic and all were discharged for occasional periodic review at that centre. However, on the basis of a recurrence of symptoms within an eighteen month to two year period, five such patients returned for urgent review, were re-biopsied and all had malignant bladder disease (Table 1). We believe that MCM has a prognostic indication for patients who in the past have been biopsy negative but MCM positive and that there may be value both in terms of bladder cancer outcomes and improved patient management for such patients.

TABLE 1

MCM/TCC/002: MCM Positive; Biopsy negative during the study

| S. No | Study Number | Cohort | MCM cell count | Follow-up |
|---|---|---|---|---|
| 1 | 3 | CS | 200 | Malignant |
| 2 | 29 | CS | 1000 | Malignant |
| 3 | 65 | CS | 2000 | Malignant |
| 4 | 1017 | CS | 3000 | Malignant |
| 5 | 14 | CS | 300 | Malignant |

The invention claimed is:

1. A method of detecting a subject suffering from, or at risk of suffering from, bladder cancer, the method comprising
    i) providing a urine sample isolated from a subject;
    ii) isolating cells from said sample to provide a cell sample;
    iii) contacting the sample with a specific binding member capable of binding to a minichromosome maintenance 2 (MCM2) polypeptide;
    iv) determining the binding of said specific binding member to the cell sample;
    v) counting those cells in said cell sample which bound to said specific binding member to provide a cell count; and,
    vi) determining, based on the cell count, whether the subject has, or is at risk of having, bladder cancer;
    wherein said determining step (vi) is based upon a measurement of MCM2 labelled cells relative to a threshold number, wherein said measurement above or equal to said threshold is indicative of bladder cancer or a risk of bladder cancer, and wherein the threshold number is about 30 to 50 cells or about 50 to 200 cells when the subject has previous evidence of bladder cancer.

2. The method of claim 1, wherein the subject presents with symptoms associated with bladder cancer.

3. The method of claim 2 wherein the symptoms of bladder cancer include haematuria.

4. A method of detecting bladder cancer in a subject who has a previous occurrence of bladder cancer or has relapsed, the method comprising:
    i) providing a urine sample isolated from a subject;
    ii) isolating cells from said sample to provide a cell sample;
    iii) contacting the sample with a specific binding member capable of binding to a minichromosome maintenance 2 (MCM2) polypeptide;
    iv) determining the binding of said specific binding member to the cell sample;
    v) counting those cells in said cell sample which bound to said specific binding member to provide a cell count; and,
    vi) determining, based on the cell count, whether the subject has, or is at risk of having, a recurrence of bladder cancer;
    wherein said determining step (vi) is based upon a measurement of MCM2 bound cells relative to a threshold number, wherein said measurement above or equal to said threshold is indicative of bladder cancer or a risk of recurrence of bladder cancer and wherein the threshold number is about 50 to 200 cells.

5. The method of claim 1 wherein the cells are isolated from the sample by filtration of the body fluid sample.

6. The method of claim 1 wherein the specific binding member is an antibody, or fragment thereof.

7. The method of claim 6 wherein the antibody is a monoclonal antibody.

8. The method of claim 1 wherein the cell count is determined by flow cytometry.

9. The method of claim 1 wherein the cell count is determined using an automated cell counter.

* * * * *